United States Patent
Thompson et al.

(10) Patent No.: US 9,226,661 B2
(45) Date of Patent: Jan. 5, 2016

(54) LASER SPECKLE IMAGING SYSTEMS AND METHODS

(75) Inventors: Oliver Bendix Thompson, Lower Hutt (NZ); Michael Kenneth Andrews, Wellington (NZ)

(73) Assignee: INDUSTRIAL RESEARCH LIMITED, Lower Hutt (NZ)

(*) Notice: Subject to any disclaimer, the term of this patent is extended or adjusted under 35 U.S.C. 154(b) by 1009 days.

(21) Appl. No.: 12/667,792

(22) PCT Filed: Jul. 7, 2008

(86) PCT No.: PCT/NZ2008/000161
§ 371 (c)(1),
(2), (4) Date: May 5, 2010

(87) PCT Pub. No.: WO2009/008745
PCT Pub. Date: Jan. 15, 2009

(65) Prior Publication Data
US 2011/0013002 A1  Jan. 20, 2011

Related U.S. Application Data

(60) Provisional application No. 61/035,193, filed on Mar. 10, 2008.

(30) Foreign Application Priority Data

Jul. 6, 2007 (NZ) ........................ 556379

(51) Int. Cl.
*H04N 7/18* (2006.01)
*G06T 7/00* (2006.01)
(Continued)

(52) U.S. Cl.
CPC ............ *A61B 5/0059* (2013.01); *A61B 5/0066* (2013.01); *A61B 5/0261* (2013.01);
(Continued)

(58) Field of Classification Search
CPC .. A61B 5/0059; A61B 5/0066; A61B 5/0261; A61B 5/444; A61B 5/445; A61B 5/7257; A61B 5/7275; A61B 2560/0233; G01N 2021/479; G01N 21/47
USPC ............................................. 348/77; 382/128
See application file for complete search history.

(56) References Cited

U.S. PATENT DOCUMENTS 4,109,647 A   8/1978   Stern
4,950,070 A   8/1990   Aizu
(Continued)

FOREIGN PATENT DOCUMENTS

WO   2005/051190 A1   6/2005
WO   2006/111836 A1   10/2006
WO   2006/111909 A1   10/2006

OTHER PUBLICATIONS

Bonner and Nossall, "Model for laser Doppler measurements of blood flow in tissue", Applied Optics 20:2097-2107 (1981).
(Continued)

*Primary Examiner* — Tat Chio
*Assistant Examiner* — Nguyen Truong
(74) *Attorney, Agent, or Firm* — Dann, Dorfman, Herrell and Skillman, P.C.

(57) ABSTRACT

An apparatus and method for measuring perfusion in a tissue. The method comprising the steps of recording images of the tissue under laser light, calculating a plurality of contrast images from the plurality of images of the tissue, determining a power spectrum of scattered light from the plurality of contrast images, and determining perfusion from the power spectrum. The apparatus comprises a digital video camera, a laser light source, and a processor arranged to operate the camera to produce a plurality of images with different exposure times, receive the plurality of images from the camera and process the images to determine a power spectrum and determine perfusion from the power spectrum.

29 Claims, 20 Drawing Sheets

(51) Int. Cl.
  *A61B 5/00* (2006.01)
  *A61B 5/026* (2006.01)
  *G01N 21/47* (2006.01)

(52) U.S. Cl.
  CPC .............. *A61B 5/444* (2013.01); *A61B 5/445* (2013.01); *G01N 21/47* (2013.01); *A61B 5/7207* (2013.01); *A61B 5/7257* (2013.01); *A61B 5/7275* (2013.01); *A61B 2560/0233* (2013.01); *G01N 2021/479* (2013.01); *G01N 2021/4735* (2013.01)

(56) References Cited

U.S. PATENT DOCUMENTS

| | | | | |
|---|---|---|---|---|
| 6,076,010 | A  * | 6/2000 | Boas et al. | 600/477 |
| 6,173,197 | B1 | 1/2001 | Boggett | |
| 6,259,936 | B1 | 7/2001 | Boggett | |
| 6,263,227 | B1 | 7/2001 | Boggett | |
| 6,944,494 | B2 * | 9/2005 | Forrester et al. | 600/478 |
| 7,113,817 | B1 * | 9/2006 | Winchester et al. | 600/476 |
| 2009/0048785 | A1 * | 2/2009 | Katzir et al. | 702/20 |

OTHER PUBLICATIONS

Briers, J.D., "Laser Doppler, speckle and related techniques for blood perfusion mapping and imaging", Physiological Measurement 22:R35-R66 (2001).

Jentink, et al., "Monte Carlo simulations of laser Doppler blood flow measurements in tissue", Applied Optics 29:2371-2381 (1990).

Parthasarathy, A., Tom, W., Gopal, A., Zhang, X., and Dunn, A., "Robust flow measurement with multi-exposure speckle imaging", Optics Express 16(3), 1975-1989 (2008).

International Search Report of International Patent Application PCT/NZ2008/000161, Dec. 5, 2008.

O.B. Thompson et al., "Spectral density and tissue perfusion from speckle contrast measurements," Proc. of SPIE, vol. 6847, Jan. 21, 2008, pp. 68472D-1-68472D-7.

Supplementary European Search Report, EP 08 79 3923, Sep. 5, 2012, 9 pages.

Notification of the Third Office Action, State Intellectual Property Office of the People's Republic of China, Appln. No. 20088010886.1, Dec. 20, 2012, 8 pages.

* cited by examiner

Figure 4. Contrast vs. exposure time.

Figure 5. Temporal autocovariance of speckle, the circles indicating points derived from speckle contrast data and the line indicating the fitted autocovariance function.

Figure 8. Triply scattered speckle experiment. A paper-covered wheel is rotated beneath a diffuser.

Figure 9. Triply scattered speckle results.

Figure 10. Covariance between two frames of image speckle: LHS with no diffuser and RHS with lightly sandblasted plastic diffuser. Target shifted 0.5 mm between frames. X and Y in pixels, covariance C in arbitrary units.

Figure 11. Depth effect test model, consisting of flow tubes in a Petri dish to be filled with tissue phantom gel.

Figure 12. Typical image of the depth effect test model. Raw image on the left, speckle contrast image on the right.

Figure 12. Depth effect results.

Figure 14. Extended blurring due to multiple scatter.

Figure 15. Contrast reduction effect of a single flow tube, semi-log scale.

Figure 16. Pulsatile component of the contrast reduction effect, showing a perforator on the forearm.

Figure 18. Perfusion index and speckle contrast changes in the back of the hand after hot water induced vasodilation.

Fig 19 Time series showing capillary pulse effect in nailbed

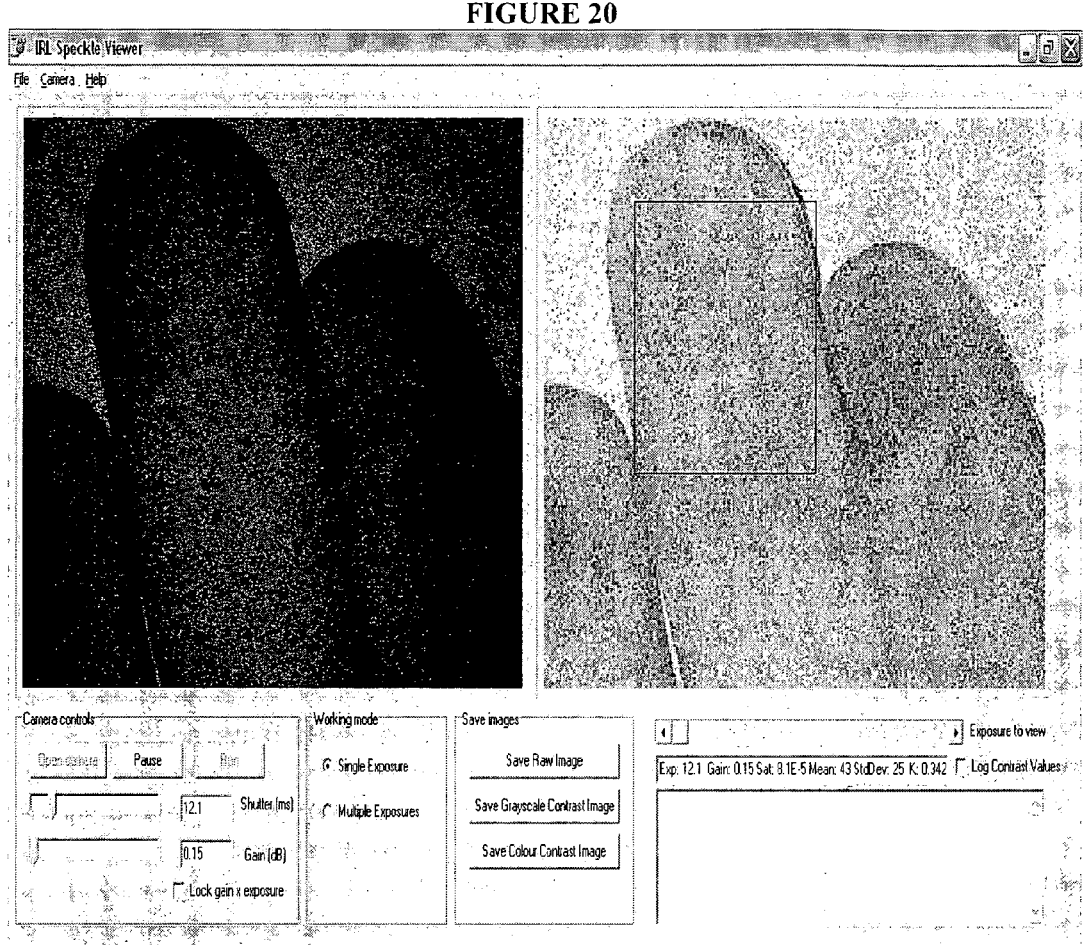
Figure 20. Screenshot of Laser Speckle Viewer software.

LASER SPECKLE IMAGING SYSTEMS AND METHODS

REFERENCE TO PRIOR APPLICATION

This application claims the benefit of U.S. Provisional Application No. 61/035,193, filed Mar. 10, 2008, the entirety of which is incorporated herein by reference.

FIELD

The field relates to methods and systems for optical imaging of particulates within a vessel or vessels, including subsurface anatomical structures and biomolecules in body tissues and, more specifically, to laser speckle imaging systems and methods, including the use of laser light to measure and quantify particulates within a vessel or vessels, including pulse, blood perfusion and real-time blood flow rates in tissue, such as dermal tissue, in subjects and patients. Also provided are various applications of such methods/systems in industrial applications and in medical diagnosis and treatment.

BACKGROUND

The following includes information that may be useful in understanding the present invention. It is not an admission that any of the information provided herein is prior art, or relevant, to the presently described or claimed inventions, or that any publication or document that is specifically or implicitly referenced is prior art.

The use of laser light to measure the speed of moving particles, particularly in gases, extends back almost to the invention of the laser. Light scattered back to a detector from a moving particle suffers a Doppler shift equal to the rate of change of the phase path between the source of light and the detector. For example, it has been shown that when examined using minute detector apertures, laser light scattered from motionless skin is Doppler shifted due to the presence of moving blood particles in the dermal layers of the body. Most of the light is returned from essentially immobile scatterers in the tissue, but a portion is returned by a multiple scatter process that involves the immobile scatterers plus scattering by one or more blood particles that flow in the network of looping capillaries within 1-2 mm of the skin surface.

The multiple scatterers complicate the analysis required to quantify such measurements in physiologically useful ways. However, it was found by Bonner and Nossall (*Applied Optics* 20:2097-2107 (1981)) that the tissue perfusion was given by the first moment of the power spectrum of the Doppler signals, and tissue perfusion can be expressed as the product of the flow velocity and the number of moving scatterers.

Laser Doppler imaging is a current optical technique that is used to evaluate blood flow changes. The output of the instrument is a two-dimensional (2D) flow-related (perfusion, speed, concentration) map over an area of up to 50×50 cm². The technique is non-invasive because it involves no physical contact. However, present commercial laser Doppler imagers do not completely fulfill all requirements imposed on them by clinical applications. They are slow, special skills are required to use them, and the interpretation of the obtained results is not always objective. Another problem with the Doppler method is that perfusion can only be measured at one site at a time. Mapping perfusion over an area is time consuming and does not take into account any rapid perfusion changes. With regard to the evaluation of perfusion or blood flow in a subject, for example in the skin of a subject, yet another issue with Doppler imaging is the fact that the subject, e.g., the skin or a body part under evaluation, must remain motionless. Thus, commercial laser Doppler imagers and the technique itself are mainly used in medical research projects but not often in clinical practice, despite the tremendous potential of laser Doppler imaging in the medical field. Currently, the two main optical techniques for in vivo monitoring of blood flow are laser Doppler flowmetry and laser speckle contrast imaging.

A speckle pattern is a random intensity pattern produced by the mutual interference of a set of wavefronts. When a surface is illuminated by a light wave, according to diffraction theory, each point on an illuminated surface acts as a source of secondary spherical waves. The light at any point in the scattered light field is made up of waves that have been scattered from each point on the illuminated surface. If the surface is rough enough to create pathlength differences exceeding one wavelength, giving rise to phase changes greater than $2\pi$, the amplitude, and hence the intensity, of the resultant light varies randomly. If light of low coherence (i.e., made up of many wavelengths) is used, a speckle pattern will not normally be observed, because the speckle patterns produced by individual wavelengths have different dimensions and will normally average one another out. This phenomenon has been investigated by scientists for many years, but speckles have come into prominence since the invention of the laser and there are a variety of applications. A familiar example is the random pattern created when a laser beam is scattered off a rough surface. The speckle effect is a result of the interference of many waves having different phases, which add together to give a resultant wave whose amplitude, and therefore intensity, varies randomly. If each wave is modeled by a vector, then it can be seen that if a number of vectors with random angles are added together, the length of the resulting vector can be anything from zero to the sum of the individual vector lengths.

Laser speckle patterns are produced by illuminating the object under test with coherent light. Speckle is the grainy appearance produced by interference between path lengths which differ randomly due to microscopic surface roughness, and may be far field speckle or image speckle. Far field speckle describes the speckled nature of the illumination at some distance from a laser spot shone on a surface, and image speckle describes the speckled appearance of an object illuminated with an expanded laser beam, as imaged by some optical system such as a camera or human eye. Laser speckle contrast imaging uses the image speckle effect, in which the pixels in an image of a uniform surface show intensities in a distribution from black to white. As the object under test moves the speckle pattern translates or changes; at any particular point, the measured intensity fluctuates with object movement.

In a system of perfusion estimation, laser speckle is used to produce full field images of relative motion. Equivalent to the Doppler shift seen at a point, the laser speckle pattern "twinkles" in space because of the light scattered by the moving blood particles when the target is living skin. The greater the rate of twinkling, the more the speckle becomes blurred in an image recorded over a finite time. This twinkling is sometimes termed "biospeckle," and the blurring is conventionally quantified by a contrast parameter K, where K is the ratio of the standard deviation of the light intensity to the mean intensity i.e.

$$K = \frac{\sigma_s}{\bar{I}}$$

where the subscript s denotes spatial variation.

Speckle images of living biological tissues such as skin show a rapidly changing speckle pattern, in contrast to the static speckle pattern produced by a stationary non-living object. This biospeckle effect is due to the scatter from moving cells, such as red cells in flowing blood, relative to the fixed scatterers as such the tissue. The spectrum of this fluctuation is determined by the number and speed of the moving particles.

The fluctuation rate can be measured indirectly by calculating the contrast over small areas of a speckle image taken at some appropriate finite exposure: if the fluctuation period at a certain point in the image is short enough compared to the exposure time, the speckle fluctuations will be blurred. Low contrast areas of the image indicate a high fluctuation rate, hence high rates of cell movement. This phenomenon has been used to produce various similar laser speckle imaging systems. These systems are sensitive to relative tissue perfusion, a measure of blood flow proportional to the product of the speed and concentration in tissue of flowing blood cells. However, the challenge for laser speckle techniques is determining a quantitative measurement of perfusion from the speckle statistics. Notwithstanding opporunities around real-time visualization of speckle contrast, real-time quantitative analysis has hitherto been lacking Thus, perfusion—blood flow in tissues—can be measured using laser Doppler techniques or laser speckle contrast imaging. Laser Doppler and laser speckle methods essentially measure the same physical effect, though they use different measurement techniques and interpretations. Doppler methods measure perfusion from the first moment of the power spectrum of the fluctuations in light returned from a small area of the tissue (Briers, J. D., "Laser Doppler, speckle and related techniques for blood perfusion mapping and imaging" *Physiological Measurement* 22:R35-R66 (2001)), which has been shown to be linearly related to blood flow by calculation and in vitro experiments (Bonner and Nossal, "Model for laser Doppler measurements of blood flow in tissue" *Applied Optics* 20:2097-2107 (1981) and modelling (Jentink, et al., "Monte Carlo simulations of laser Doppler blood flow measurements in tissue" *Applied Optics* 29:2371-2381 (1990)). This was initially a single point measurement, using a probe to measure the spectrum returned from a small volume of tissue illuminated by laser light, though an image of an area of tissue can be produced by scanning the measurement point. Laser speckle perfusion measurements, on the other hand, use the spatial statistics of the fluctuating laser speckle pattern (biospeckle) recorded by a camera at a finite exposure to generate a map of relative perfusion. Laser speckle perfusion is an area measurement by nature, producing an image with every exposure, by comparison with laser Doppler images produced by scanning. As noted above, a current challenge for laser speckle techniques is determining a quantitative measurement of perfusion from the speckle statistics.

Thus, it will be appreciated that laser Doppler and laser speckle imaging are two optical non-invasive techniques that are used to obtain 2D maps of blood flow in biological tissues, and each of these existing techniques has benefits and drawbacks for measuring the blood flow. Laser speckle contrast imaging can be seen as a real-time imaging technique, but the interpretation of its response to changes in flow parameters such as speed and concentration is problematic. In contrast, laser Doppler imaging has clearer biological interpretation but it is not a real-time technique.

In one embodiment, a new laser speckle imaging system takes speckle contrast measurements over multiple exposure times and uses temporal autocorrelation information derived from speckle contrast measurements to provide spectral information and a perfusion index that is precisely equivalent to that produced in laser Doppler methods.

In another embodiment, numerically constructed autocorrelation data are approximated by mathematical functions with an adjustable parameter $\tau_c$. The speckle contrast information is determined from each of the plurality of images and a plurality of contrast images are formed therefrom. From the plurality of contrast images, one or more parameters of a temporal autocorrelation function representative of tissue speckle are derived. A perfusion value of a fluid moving through the medium is determined from the one or more parameters.

The various embodiments of the invention described and claimed herein thus overcome the drawbacks of laser speckle imaging and provide particulate flow and velocity images in real time over a scanned area that are equivalent to laser Doppler images taken at a static single point.

BRIEF SUMMARY

The inventions described and/or claimed herein have many attributes and embodiments including, but not limited to, those set forth or described or referenced in this Brief Summary. It is not intended to be all-inclusive and the inventions described and/or claimed herein are not limited to or by the features or embodiments identified in this Brief Summary, which is included for purposes of illustration only and not restriction.

It is the object of the present invention to provide an improved or alternative method of measuring particulate flow and velocity in a vessel. The invention may be used, for example, to measure perfusion or blood flow in a tissue of a subject, including the skin.

In one aspect an embodiment of the invention comprises a method of measuring perfusion or blood flow in the skin comprising the steps of recording a plurality of images of the skin under laser light with different exposure times over a short time frame, determining the power spectrum of scattered light from the plurality of images and determining perfusion from the power spectrum.

In one embodiment, the exposure times range between 0.1 milliseconds (ms) and 100 ms. In a preferred embodiment, the exposure times range between 1 ms and 50 ms.

In one preferred embodiment, the time frame over which exposures are taken is less than 2 seconds. In another more preferred the time frame over which exposures are taken is less than 0.5 seconds.

In one embodiment, the laser is a thermoelectrically cooled, 50 mW, 658 nanometer single mode diode laser from Word Star Technologies.

In one embodiment the power spectrum is determined by generating a temporal autocorrelation function from the change of spatial contrast of the speckled images with exposure time at points of interest, and converting the temporal autocorrelation function to its power spectrum. In one embodiment, the autocorrelation function is converted to its power spectrum using the Wiener Kintchine theorem.

In another embodiment, weighted moments are calculated from the power spectrum. The first moment of the power spectrum is a proportional measure of the perfusion.

In another aspect an embodiment of the invention comprises an apparatus for measuring perfusion comprising a digital video camera (which may be, for example, a monochrome or a color camera operating in monochrome mode), a laser light source, and a processor arranged to operate the camera to produce a plurality of images with different exposure times, receive the plurality of images from the camera and process the images to determine the power spectrum of scattered light from the images at each point or selected points and determine perfusion from the power spectrum by computing its first moment. In other embodiments, a color camera may be used, but the speckle contrast calculations do not use the chrominance components of the signals.

In one preferred embodiment, the laser operates in a single mode to ensure maximum contrast in the speckle and consistent contrast in the image of a static object.

In one preferred embodiment, a computer or other programmed device controls the camera gain and exposure times, and receives and processes the data to provide a desired output.

In one preferred embodiment, the camera and laser source are stably mounted (e.g., to a tripod or stand) to eliminate vibrational motion. Optionally, the camera may be provided with an image stabilization function to compensate for camera vibration. Additionally, the subject being imaged may be stabilized or supported to eliminate subject motion.

Yet another aspect concerns computer program products comprising a computer useable medium having computer program logic recorded thereon for controlling the apparatus to collect the speckle images at a plurality of different exposure times, and to extract flow information from the exposure-dependent contrast measurements. Such computer program logic preferably comprises computer program code logic configured to perform a series of operations, including receiving data from the camera, determining a set of temporal autocovariance data for each of a plurality of regions.

In one preferred embodiment, for each area of interest the speckle contrast K is calculated for each of the exposure values. The product of exposure time T times $K^2$ is then formed. Statistical theory teaches that the slope of this quantity with respect to exposure time T is the temporal autocorrelation function of the speckle intensity. The power spectrum is then computed from the Fourier transform of the autocorrelation function, and the perfusion from the first moment of this spectrum.

---

Stepwise, following capture of a set of frames.
For each area of interest:
//calculate $TK^2$ values
For i from 0 to number of exposures-1 do
Begin
    Calculate K and $TK^2$;
    Record $TK^2$;
End;
//calculate slopes
For i from 1 to number of exposures-1 do
Begin
    Calculate slope between adjacent $TK^2$ values;
End;
//calculate power spectrum
Calculate FFT of slope record;
//calculate perfusion index
Take first moment of absolute FFT results;

---

Another preferred embodiment arises from the discovery that the autocorrelation function may be approximated by an analytic expression, described by a single time constant $\tau_c$, which has a simple integral. This integral is fitted to the measured data set $TK^2$ to derive $\tau_c$, which then defines the actual autocorrelation function. The power spectrum of the fluctuations may be obtained from the FT of this autocorrelation function, but the first moment, representing the perfusion, can be derived from a pre-computed look-up table or interpolation function.

---

Stepwise, following capture of a set of frames.
For each area of interest:
//calculate $TK^2$ values
For i from 0 to number of exposures-1 do
Begin
    Calculate K and $TK^2$;
    Record $TK^2$;
End;
//find $\tau_c$ representing the autocorrelation function.
Least squares fit autocorrelation function integral to $TK^2$ values;
Compute best-fit $\tau_c$;
Compute power spectrum from autocorrelation function;
Extract perfusion value from look up table or interpolation routine;

---

In still other aspects, embodiments of the invention have clinical application for use in evaluating subjects and/or their conditions. By way of example, the laser speckle imaging devices and methods in some embodiments of the invention may be used to measure blood perfusion and flow, including cortical vascular blood flow, cerebral blood flow, ocular blood flow, retinal blood flow, and blood perfusion and flow in other tissues, such as skin.

Various embodiments of the present invention also provide methods and apparatus for assessing a patient's vascular health by evaluating or monitoring hemodynamic and/or perfusion parameters. The laser speckle imaging devices and methods of an embodiment of the invention can be used, for example, to evaluate wounds, including acute and chronic wounds, and wound status. They may also be used to evaluate diabetes and the diabetic condition, and to evaluate cardiovascular and cerebrovascular disease.

Thus, in another aspect one embodiment of the invention provides a modular functional vascular status assessment apparatus, which comprises a CPU in electrical communication with and controlling a laser and an image capture device suitable for obtaining and storing speckle images, the CPU being capable of processing the speckle images by finding a temporal autocorrelation function to calculate a power spectrum of scattered light from the speckle images and obtain a perfusion index.

In one embodiment, the image capture device in the apparatus may be controlled to capture multiple images over a range of exposure times of less than 100 milliseconds. In another embodiment, the apparatus further comprises a monitor for viewing speckle images.

In yet another embodiment, the apparatus CPU is programmed to perform a vascular status assessment. The vascular status assessment may be a hemodynamic assessment (including blood flow), a perfusion index, and/or perfusion map.

In still another embodiment, the CPU may comprise one or more sets of normohemodynamic and/or normoperfusion data and be programmed to compare the normohemodynamic and/or normoperfusion data to an obtained hemodynamic and/or perfusion index.

In other embodiments, the apparatus CPU is programmed to perform a pulse wave form analysis, and/or to determine any of a flow velocity, a pulse wave velocity, and a contralateral vascular response.

In another aspect one embodiment of the invention provides a computer implemented method for assessing cardiovascular risk, comprising receiving results from one or more vascular functional assessments performed on an individual using an apparatus as describes above and elsewhere herein; placing the results of the functional assessments into a computational dataset corresponding to the individual; receiving a status for each of a plurality of epidemiologic risk factors; placing the status of each epidemiologic risk factor into the computational dataset corresponding to the individual; and computing a combined functional and epidemiologic relative risk for the individual from the dataset corresponding to the individual. In certain embodiments of this method, the one or more vascular function assessments may be one or more of a perfusion index, a perfusion map, a pulse wave form analysis, a vascular flow velocity, a vascular pulse wave velocity, and a contralateral vascular response.

In another embodiment, the computer implemented method may further comprise receiving results from one or more structural assessments on the individual; placing the results of the one or more structural assessments into the computational dataset corresponding to the individual; and computing a combined functional, epidemiologic, and structural relative risk for the individual from the dataset corresponding to the individual. Structural assessments include determination of pathologic changes including one or more of: increased intima medial thickness, atherosclerotic plaque formation and calcium deposits in at least one vascular bed.

In another embodiment, the computer implemented method further comprises receiving results from one or more hematological assays of a status of blood oxygenation or glycemia on the individual; placing the results of the one or more hematological assays into the computational dataset corresponding to the individual; and computing a combined functional, epidemiologic, and hematological relative risk for the individual from the dataset corresponding to the individual.

In another aspect one embodiment of the invention provides a computer implemented method for determining a neurovascular status for an individual, comprising receiving results from one or more assessments performed on an individual using an apparatus as described above and elsewhere herein to assess local blood flow on a test site on the individual, and establishing a neurovascular assessment for the individual based on a blood flow response at the test site.

In another aspect one embodiment of the invention provides a computer implemented method for determining a microcirculation status for an individual with diabetes comprising using an apparatus as described above and elsewhere herein to assess local blood flow on a test site on the individual, and establishing a microcirculation assessment for the individual based on blood flow perfusion at the test site.

In another aspect one embodiment of the invention provides a computer implemented method for monitoring the progress of coagulating and cross-linking processes in translucent materials such as paints, epoxies and resins by measuring the reduction in the Brownian motion of scattering particles using the apparatus as described above.

These and other aspects of the present inventions, which are not limited to or by the information in this Brief Summary, are provided below. Other and further aspects, features, and advantages of the present invention will be apparent from the following description of the inventions and presently preferred embodiments given for the purpose of disclosure.

BRIEF DESCRIPTION OF DRAWINGS

The above-recited features, advantages and objects of certain embodiments of the invention, as well as others which will become clear, may be further understood together with the more particular descriptions of some embodiments of the invention briefly summarized above by reference to the appended drawings. These drawings form a part of the specification. It is to be noted, however, that the appended drawings illustrate preferred embodiments of the invention and therefore are not to be considered limiting in their scope. Thus, the invention will be further described by way of example only and without intending to be limiting with reference to the following drawings, wherein

FIG. 20 shows a screenshot of example speckle contrast viewer software.

DETAILED DESCRIPTION

Anomalous changes in peripheral blood flow are known to be a good indicator of various health disorders in the human organism. Measurement of the velocity of blood flow, has now become a potential diagnostic method for detecting or evaluating diseased portions in the circulatory system represented, for example, by diabetes, by vascular stenosis and thrombosis, or for investigating vital reactions occurring in consequence of administration of treatments and medicines.

The inventors have developed an improved laser speckle imaging system that can be used for real-time imaging of the motion of particulates within a vessel or vessels that are penetrable by a laser light source. Using speckle contrast measurements over 5 decades of exposure time, for example, the inventors have shown that a temporal autocorrelation function, and hence spectral information and a perfusion index precisely equivalent to that produced in Doppler methods, can be derived from speckle measurements.

The inventors have also discovered that the autocorrelation data are well approximated by a simple but non-exponential function which is parametric in a characteristic time $\tau_c$. A perfusion index can be found by determining $\tau_c$ from a small number of speckle measurements at appropriate exposures. This is illustrated in the Examples by measurement of perfusion recovery following an induced change in perfusion. Uses of the laser speckle imaging system of embodiments of the invention include blood-flow and blood perfusion measurements and imaging in a tissue or body part, amongst others.

Figure 1:
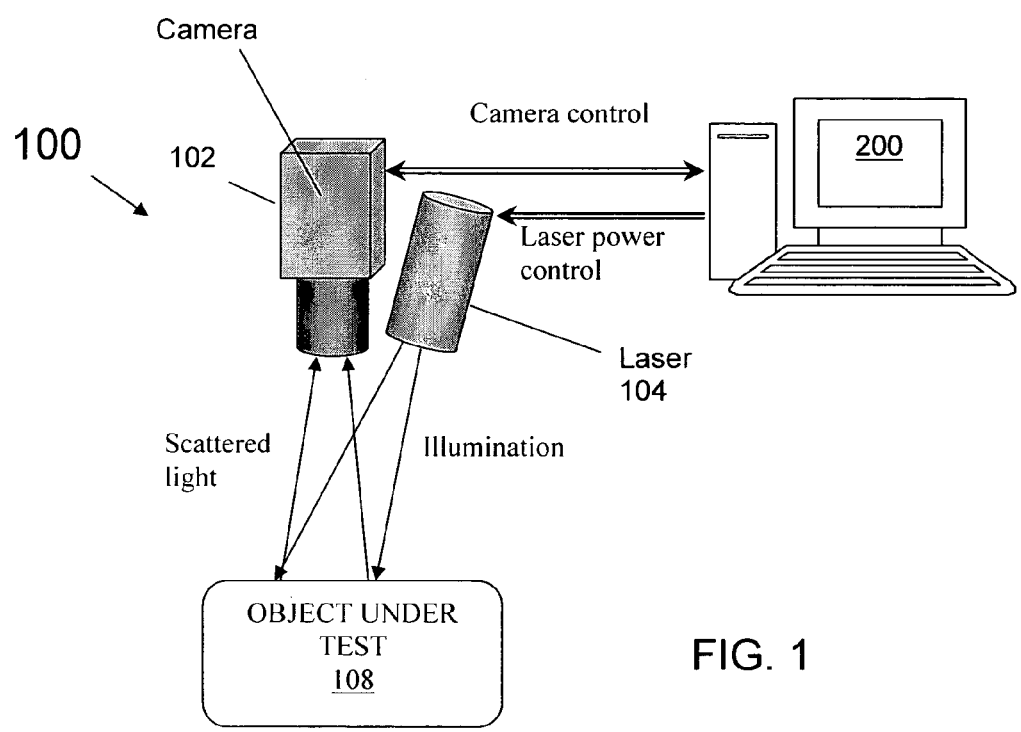
FIG. 1 illustrates one example of a perfusion measurement system.

Devices useful in some embodiments of the invention have a laser light source, an image capture device, and a device for data storage and/or manipulation and display, and may be described in reference to the Figures. In one example, a 658 nanometer laser is used as the light source. Such light penetrates tissue and scatters well from red blood cells, for example. In other embodiments, different laser wavelengths may be used to control the volume of tissue probed. One laser speckle imaging system is shown in FIG. 1. The object under examination is illuminated with coherent light using an expanded laser beam. Images of the illuminated area are captured using a digital video camera and analyzed using a computer or other programmed device.

An improved system and method for obtaining a perfusion measurement of fluid perfusing through a medium is now described. FIG. 1 illustrates one example of a perfusion measurement system 100. As shown in FIG. 1, perfusion measurement system 100 includes a digital video camera 102, an illuminating laser source 104, and a computer 200.

Camera 102 may be a charged coupled device ("CCD") camera. An example of such a camera includes, but is not limited to, the XCD-SX910 made by Sony Electronics, Inc. Camera 102 may have a variable electronic gain and an exposure time that may be controlled by computer 200. In some embodiments, camera 102 may have a resolution of 1200 by 960 pixels and have an exposure time that may be varied between 10 μs to 17.5 seconds. Camera 102 may be configured to operate in monochrome mode. In some embodiments, camera 102 may be configured with a lens and filter. An example of such a lens includes, but is not limited to, a lens having a 75 mm focal length. Additionally, a variable gain adjustment on the camera can allow collection of images with different exposure lengths at a fixed aperture without saturating the sensor.

Laser light source 104 may be a laser of typically 50 mW power, preferably with variable output power, to provide flexibility in either having sufficient optical power to illuminate a large area of the medium, or to obtain sufficient light when acquiring images with short exposure times. To avoid mode-hopping, a thermally stabilized, single mode laser may be implemented. An example of such a laser is the TECRL series laser available from World Star Technologies having a power output of 50 mW at 658 nm. In one embodiment, the laser light source 104 provides a laser light having a wavelength within the red spectrum, e.g., a wavelength of approximately 635 nm to approximately 690 nm, although other wavelengths may be used.

In one embodiment, laser light source 104 and camera 102 may be stably mounted to remove vibrational blurring of the acquired images. Laser light source 104 and camera 102 may be mounted such that the camera 102 is focused on the area of the surface of the medium 108, which may be the skin of a patient, where incident rays from laser light source 104 contact the surface of the medium 108.

The above system may be used to determine fluid perfusing throughout medium 108, e.g., blood flowing through capillaries in skin, by taking a plurality of images of a laser light on a surface of the medium. The images may be acquired at different exposures. An example range of exposure times include, but is not limited to, from 0.001 ms to 1 second. Preferably, the images are acquired using an exposure time of 0.1 ms to 100 ms and more preferably with an exposure time of 1 ms to 20 ms. The varied exposure times produce a range of speckle contrasts at points in each image according to the perfusion of fluid through the medium at that point.

The speckle size in an image speckle is estimated by the following formula:

$$S \approx 1.2(1+M)\lambda F$$

Where, S is the speckle size; M is the imaging magnification; $\lambda$ is the laser wavelength; and F is the F-stop number of the imaging lens. In one embodiment, speckle images are taken at a fixed lens aperture chosen to maintain a constant speckle size comparable or larger than the camera pixel size. This ensures high speckle contrast for a static object. The camera gain may be varied with exposure time if exposures with varying exposures are desired to ensure the images use the full dynamic range of the camera 102. In some embodiments, changes in the gain of camera 102 may be replaced or augmented by placing different attenuating filters in front of the lens. Alternatively, the power of the laser light source 104 may be modulated as the exposure time varies, for example by its inbuilt circuitry or by an Electro-Optic Modulator (EOM) (e.g. Thor Labs, Newton, N.J., U.S.A.).

A wider exposure variation may be achieved by using a part of the dynamic range of the camera 102 with short exposure times. This is achieved by using a camera with more grayscale bits to ensure that the less intense exposures are adequately encoded.

In use, the device is typically associated with a computer or programmed memory. In some embodiments, the computer is used for receiving, storing, analyzing, and outputting the results of the speckle measurements. In some embodiments, the computer also controls the operation of the laser and/or the camera, to take the measurements.

Computer 200 may be any type of computer having a central processing unit (CPU) such as a personal computer, laptop, or mainframe. Additionally, computer 200 may be configured to run any type of operating system including, but not limited to, Microsoft® Windows, Linux, Mac OS X, FreeBSD®, and the like. The computer 200 may be configured with one or more of a variety of peripheral ports such as, for example, a PS/2 port, an RS232 or serial port, a USB port, an IEEE 1284 or parallel port, a Peripheral Component Interconnect (PCI) slot, and an IEEE 1394 port to which camera 102 and laser 104 may be connected.

Figure 2:
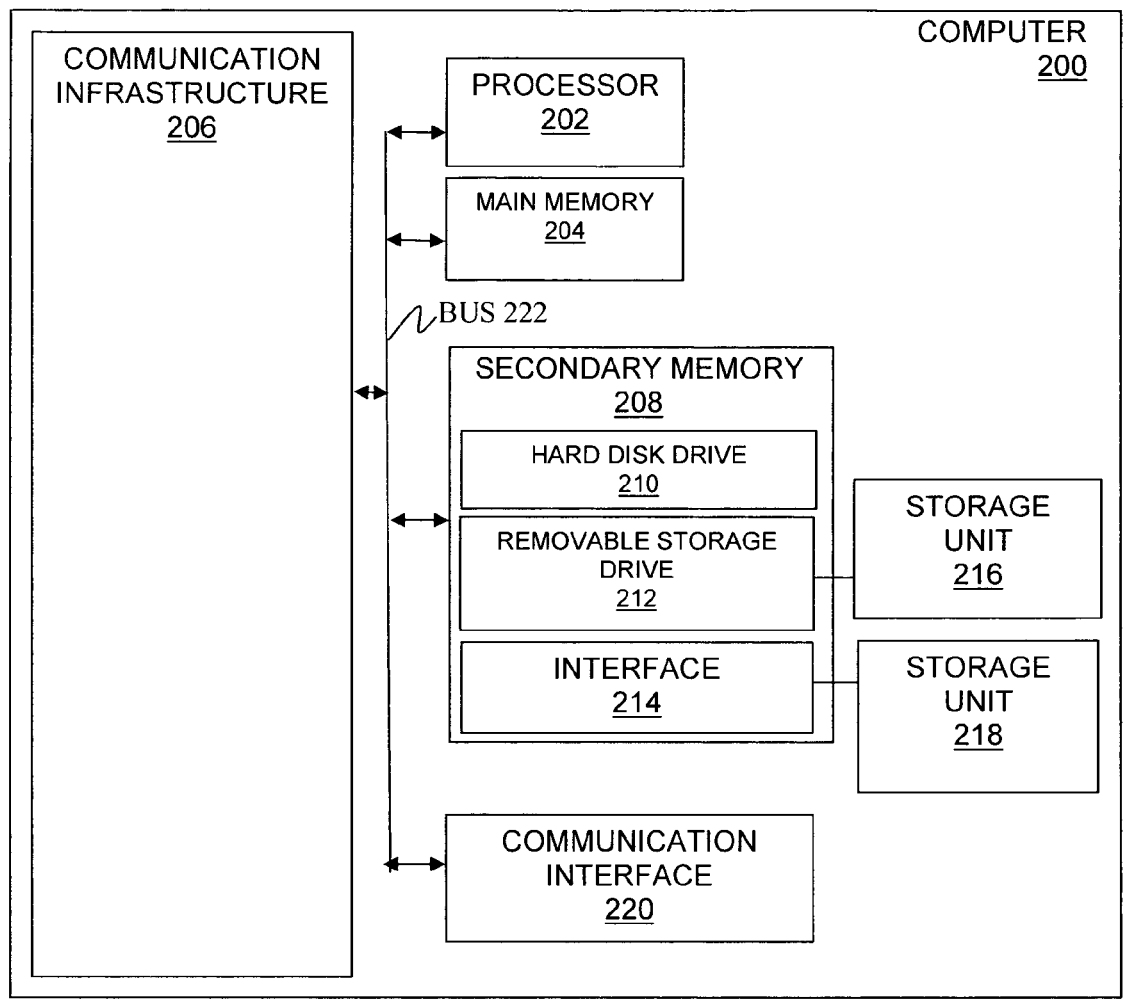
FIG. 2 illustrates one example of a computer system useful in embodiments of the invention.

As shown in FIG. 2, computer 200 may include one or more processors 202, which may be connected to a communication infrastructure 206 (e.g., a communications bus, cross-over bar, or network). Computer 200 may include a main memory 204, such as a random access (RAM) memory, and may also include a secondary memory 208. The secondary memory 208 may include, for example, a hard disk drive 210 and/or removable storage drive 212, representing a floppy disk drive, a magnetic tape drive, an optical disk drive, etc. The removable storage drive 212 may read from and/or write to a removable storage unit 216. Removable storage unit 216 may be a solid state drive, external hard disk drive, flash drive, floppy disk, magnetic tape, optical disk, ZIP™ drive, or the like, which may written to and read by removable storage drive 212. Removable storage unit 212 may include a computer usable storage medium having stored therein computer software and/or data.

In some embodiments, secondary memory 208 may include other similar devices for allowing computer programs or other instructions to be loaded into computer 200. Such device may include, for example a removable storage unit 218 and an interface 218. An example of such a device and socket includes, but is not limited to, a USB flash drive and associated socket. Other removable storage units 218 and interfaces 214 that allow software and data to be transferred from the removable storage unit 218 to computer 200 may be used.

In alternative embodiments, secondary memory 208 may include other similar means for allowing computer programs or other instructions to be loaded into computer system 200. Such means can include, for example, a removable storage unit 216 and an interface 214. Examples of such can include a program cartridge and cartridge interface (such as that found in video game devices), a removable memory chip (such as an EPROM, or PROM) and associated socket, and other removable storage units 218 which allow software and data to be transferred from the removable storage unit to computer system 200.

Computer 200 may also include a communications interface 220 that data to be transferred between computer 200 and external devices, such as, for example, camera 102 and laser 104. Examples of communications interface 220 may include a modem, a network interface (such as an Ethernet card), a communications port, a Personal Computer Memory Card International Association (PCMCIA) slot, and card, etc. Software and data transferred via communications interface 220 are in the form of signals which may be electronic, electromagnetic, optical, or other signals capable of being received by communications interface 220. These signals are provided to communications interface 220 via a communications path or channel. The path or channel that carries the signals may be implemented using wire or cable, fiber optics, a telephone line, a cellular link, a radio frequency (RF) link and other communication channels.

In this document, the terms "computer program medium" and "computer usable medium" are used to generally refer to machine readable storage media such as removable storage device 216. These computer program products are means for providing software or program instructions to computer system 200. When the computer program code stored in medium 216 is executed by the processor 202, the processor performs a method for perfusion and other assessments and measurements as described herein. Thus, the processor executing the computer program code acts as a special purpose processor for performing the perfusion measurement and other operations.

In another embodiment, the elements are implemented primarily in hardware using, for example, hardware components such as programmed array logic (PALs), application specific integrated circuits (ASICs) or other hardware components. Implementation of a hardware state machine so as to perform the functions described herein will be apparent to persons skilled in the relevant art(s). In yet another embodiment, elements are implemented using a combination of both application specific hardware and computer processor equipment configured to execute software.

Data acquisition comprises initiating a series of frames at different exposures which encompass the maximum range used, computing the speckle contrast for each frame in the conventional way, then assembling for each pixel, or chosen pixel, the variation of contrast with exposure. This generates a 3-D matrix which contains the information from which the autocorrelation function at each pixel will be found and transformed to power spectra or flow parameters such as perfusion index.

Figure 3:
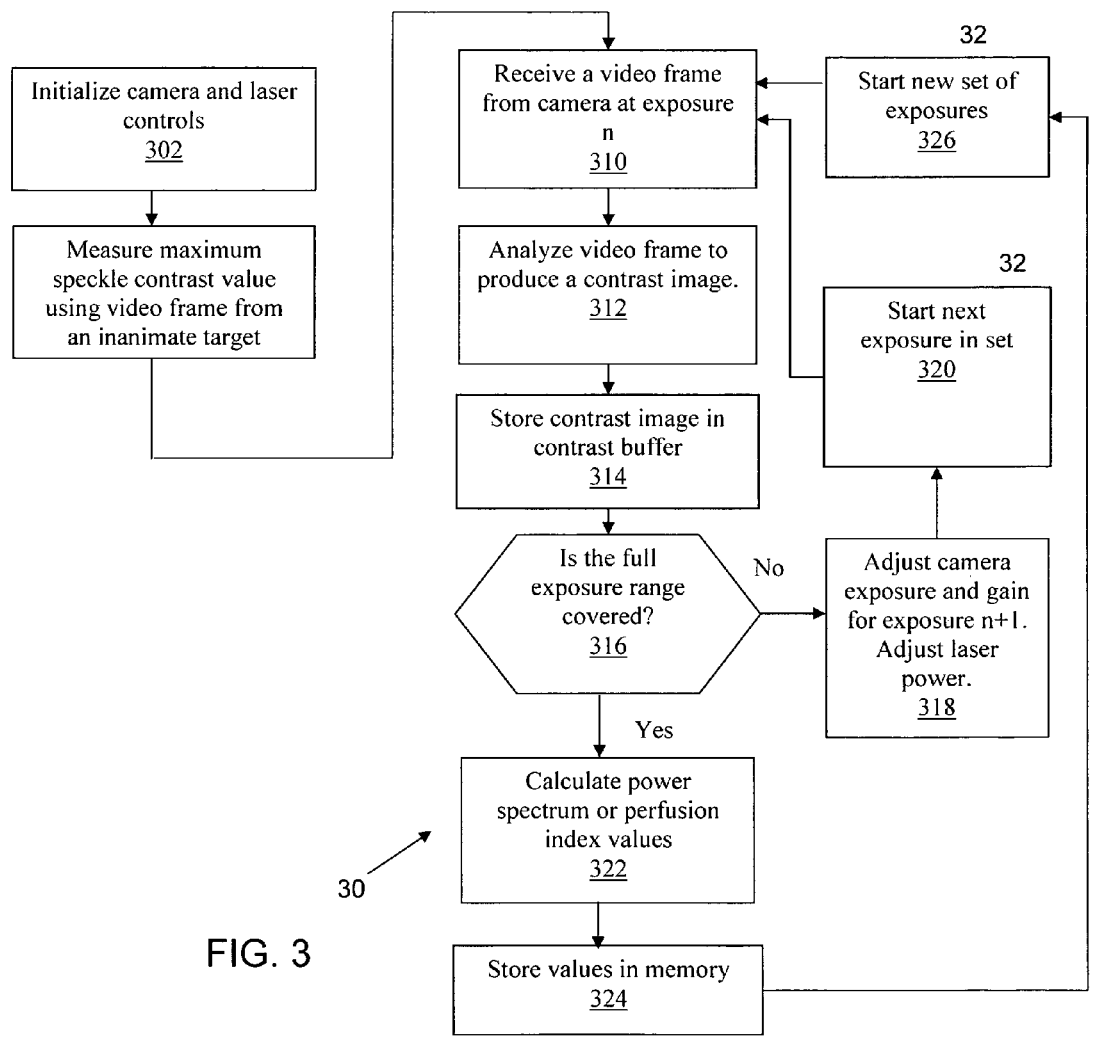
FIG. 3 is a flow diagram of one example of a method of determining the perfusion of fluid through a medium

FIG. 3 shows a flow chart diagram outlining a computer program product comprising a computer useable medium having computer program logic recorded thereon for modulating exposure times in a laser speckle imaging system of FIG. 1 using a coherent light source, typically a laser 104 such as a 50 mW, 658 nm single mode diode laser, to evaluate particle flow within a vessel by application of a temporal autocorrelation function to produce spectral information and, if desired depending on the application, a perfusion index or indication of the first moment of the power spectral density of the speckle image data.

FIG. 3 is a flow diagram of one example of a method 300 of determining the perfusion of fluid through a medium.

As shown in FIG. 3, the camera 102 and laser 104 are initialized at block 302.

At block 304, a reference video frame of an inanimate target is acquired by camera 102 and analysed to calibrate the maximum value of speckle contrast the laser will produce. The reference contrast value may be obtained using an inanimate reference surface because the contrast value for such a surface is independent of the exposure. In some embodiments, the reference value may be inferred from pre-measured optical properties of the system. These properties may include the effects of changes to an aperture and/or target ranges.

At block 310, a video frame is acquired with a first exposure, n.

At block 312, the video frame is analyzed to produce a contrast image.

At block 314, the contrast image is stored in a contrast buffer.

At decision block 316, a check is made to determine if the full exposure range has been covered.

If the full exposure range has not been covered, then the camera exposure, gain, and laser power are adjusted at block 318.

At block 320, the next exposure, n+1, in a set of exposures is begun, which includes repeating the image acquisition and analysis at blocks 310 and 312.

If the full range of exposures has been covered at block 316, then at block 322 the power spectrum and perfusion index values are calculated.

At block 324, the calculated values are then stored in a memory 204, 208.

At block 326, once the values are stored, a new set of exposures may be started.

As described herein, methods and devices for laser speckle imaging have been invented that have the quantitative advantages of Doppler measurements while keeping the real time image generation capability of speckle contrast imaging, while at the same time avoiding the disadvantages of laser Doppler. This is accomplished by methods for obtaining and analyzing a series of speckle contrast measurements over a range of exposures. The first moment of the extracted power spectrum is measured to calculate a perfusion index identical to that measured by Doppler techniques.

In one embodiment of the invention, the speckle imaging system uses a CCD camera and a laser. In one preferred embodiment, a Sony CCD camera with 4.7 µm square pixels is used, together with a World Star Technologies thermoelectrically cooled 50 mW, 658 nm single mode diode laser. The F-stop for the 75 mm camera lens is set to produce a characteristic speckle size similar to the camera pixel size, using the approximation S=1.2(1+M)λF where S is the speckle size, M is the imaging wavelength, λ the laser wavelength and F the aperture of the imaging lens. Optionally, a polarising filter is used to restore high values of contrast since multiple scatter in tissue has a depolarising effect, reducing contrast as described in Example 1. The speckle contrast K may be calculated for 5×5 pixel squares to produce each speckle contrast image and mean contrast values can be taken over large areas of the image, optionally excluding saturated or underexposed regions. Software as described herein can be used to control the electronic gain and exposure time of the camera and perform the contrast calculations, allowing measurements at a range of exposures to be taken quickly.

As noted above, to determine perfusion in tissue a series of images of the tissue in question is taken with a range of exposure times. The exposure times may range from 0.001 ms to 1 second but are typically of the order of 0.1 ms to 100 ms and ideally of the order of 1 ms to 20 ms. The exposure times produce a range of speckle contrasts at points in each image according to the perfusion at that point. At points of interest in the image the change of spatial contrast with exposure time is used to generate the temporal autocorrelation function of the light. The power spectrum can then be calculated from the autocorrelation function using the Weiner Kintchine theorem. The first moment is then calculated from the power spectrum. The first moment produces data equivalent to that produced using equivalent Doppler values. This data can be used to determine perfusion values using the techniques of Bonner and Nossall (*Applied Optics* 20:2097-2107 (1981)).

Figure 4:
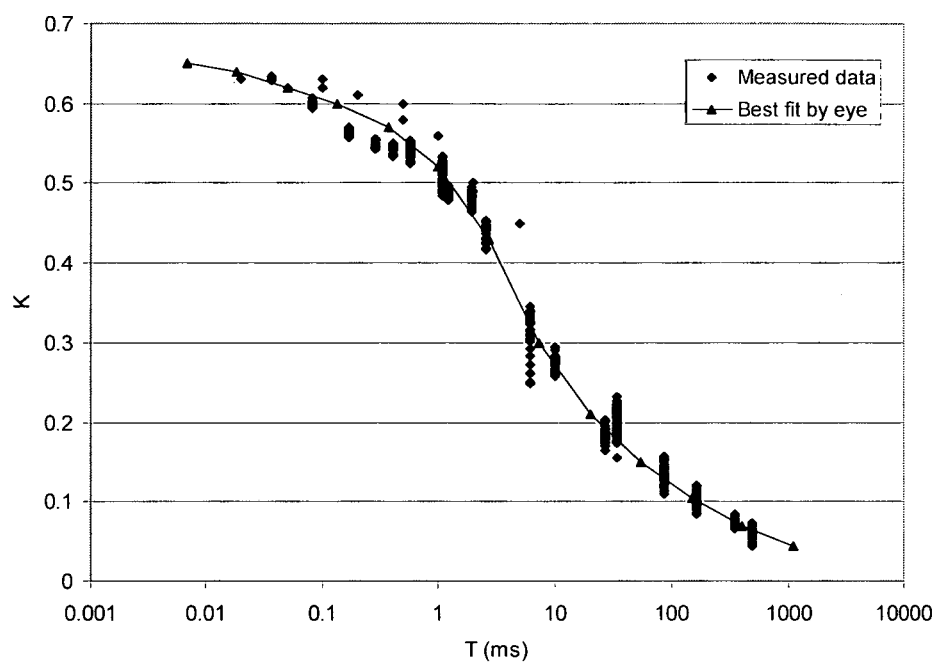
FIG. 4 is a graphical representation of contrast versus exposure time.

Because speckle patterns involving moving scatterers are dynamic, photographs or images of the patterns will become progressively blurred with increasing averaging or exposure time. The mean speckle contrast of images of the skin on the back of a hand was measured over a range of exposures from 0.02 ms to 490 ms (FIG. 4). The measured values are asymptotic to a contrast of about 0.65. Fully developed, polarised speckle, not blurred by motion, has a contrast of 1. The aperture used sets the highest spatial frequency present in the speckle, but over a single pixel there remains an intensity variation which is effectively averaged or blurred. This reduced contrast. It was confirmed that, while the same contrast (0.65) was measured in a stationary, multiply-scattering object, this contrast could be increased to approach 1 by reducing camera aperture and thus increasing the speckle size relative to a pixel, at the cost of reducing the usable exposure range for the biospeckle measurements. The non-one value of K could be corrected for using a reference value of contrast, $K_{max}$ as found at block 304 of the flow diagram FIG. 3.

The "freeze time," an exposure that will completely freeze the speckle pattern produced by living tissue very short—typically below 50 μs, for example. Any practical exposure will blur a biospeckle pattern to some degree. The sigmoid-like data of FIG. 4 show that the appropriate exposure to achieve maximum sensitivity in speckle imaging of tissue is about 3 ms, at the inflexion point of the hand-drawn curve.

Under the assumption that the speckle statistics are ergodic the spatial variance $\sigma_s^2$ measured with exposure T is linked to temporal variations at a point by $$\sigma_s^2 = \frac{1}{T}\int_0^T C_t(\tau)d\tau \qquad (1)$$

where $C_t(\tau)$ is the temporal autocovariance of a single speckle as described in Goodman, J. W., "Statistical Optics" Wiley, New York, 1985. Hence $$C_t(T) = \frac{d}{dT}T\sigma_s^2 \qquad (2)$$

The spatial contrast K can be measured, which is the standard deviation normalised by the mean intensity:

$$K = \frac{\sigma_s}{\bar{I}} \qquad (3)$$

The autocovariance function can be derived from the speckle measurements $$C_t(T) = \frac{d}{dT}TK^2\bar{I}^2 \qquad (4)$$

This function is scaled by the mean intensity squared, a constant and effectively arbitrary factor. However, a normalized version may be used in this application, the autocorrelation $R_t(T)$ which is scaled to have a value of 1 as T approaches 0 and K approaches $K_{max}$ $$R_t(T) = \frac{1}{K_{max}^2}\frac{d}{dT}TK^2 \qquad (5)$$

Figure 5:
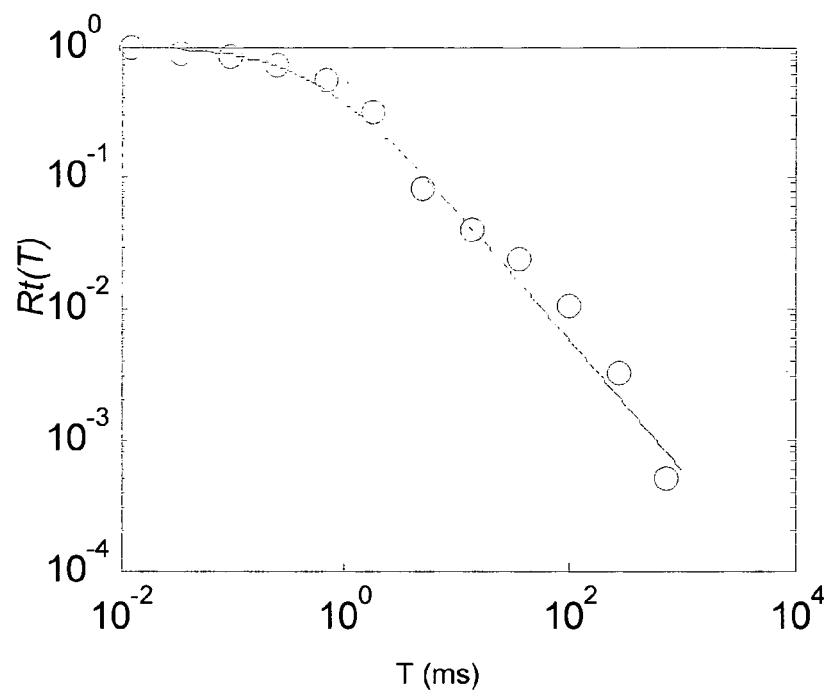
FIG. 5 provides a graphical representation of biospeckle temporal autocovariance.

The discrete data in FIG. 5 is the autocorrelation recovered, using the smoothed fit to the contrast drawn in FIG. 4. The Fourier transform of these data, by the Wiener Kintchine relation, gives the power spectrum of the speckle. In the previously known pure Doppler experiment, the power spectrum can either be computed directly from the Fourier transforms of its time series, or using the Wiener Kintchine theorem, from the Fourier transform of the autocorrelation function derived from the time series. The technique above therefore recovers precisely the same spectral information as the Doppler method. Moments of the power spectrum can therefore be taken and perfusion values can be found from the moments. See, e.g., Bonner and Nossal, supra. Perfusion values can be calculated for any given point on the image or a full-field perfusion image can be created.

Figure 6:
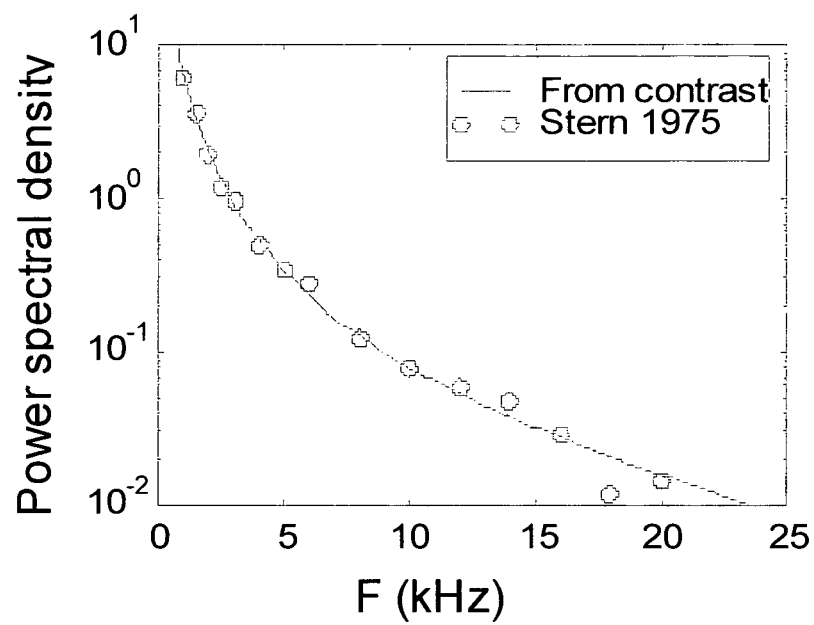
FIG. 6 illustrates the power spectral density S(f) of a photocurrent tin biospeckle.

The power spectral density S(f) of the speckle fluctuations was computed from the Fourier transform of the data in FIG. 5. This is shown in FIG. 6, together with an original spectral data set derived from Doppler measurements (Stern M. D., Nature, 254, 1975, pp 56-58). The agreement between the two datasets demonstrates that the methods of the invention are sound.

Laser Doppler measurements give direct indication of the motion of scattering particles, something not readily apparent in speckle images. Time information has been reintroduced into speckle via exposure-dependent contrast. Others have approached the extraction of particle speed indirectly by assuming that the temporal autocovariance of a single speckle has a characteristic time $\tau_c$ of the form $$C_t(\tau) = e^{-|\tau|/\tau_c}$$

Equation (1) may then be integrated giving $$K = \sqrt{\frac{\tau_c}{2T}\{1 - e^{(-2T/\tau_c)}\}}$$

which allows a value of $\tau_c$ to be extracted from a particular contrast K and exposure time T. However, the inventors have discovered that for a fixed flow, the value of $\tau_c$ found by this method is not unique and depends on the exposure time. The reason is apparent from the experimentally derived autocorrelation function (FIG. 5 and Eqn (6) below), which is only approximately exponential for times less than $\tau_c$, here 0.6 ms.

Figure 7:
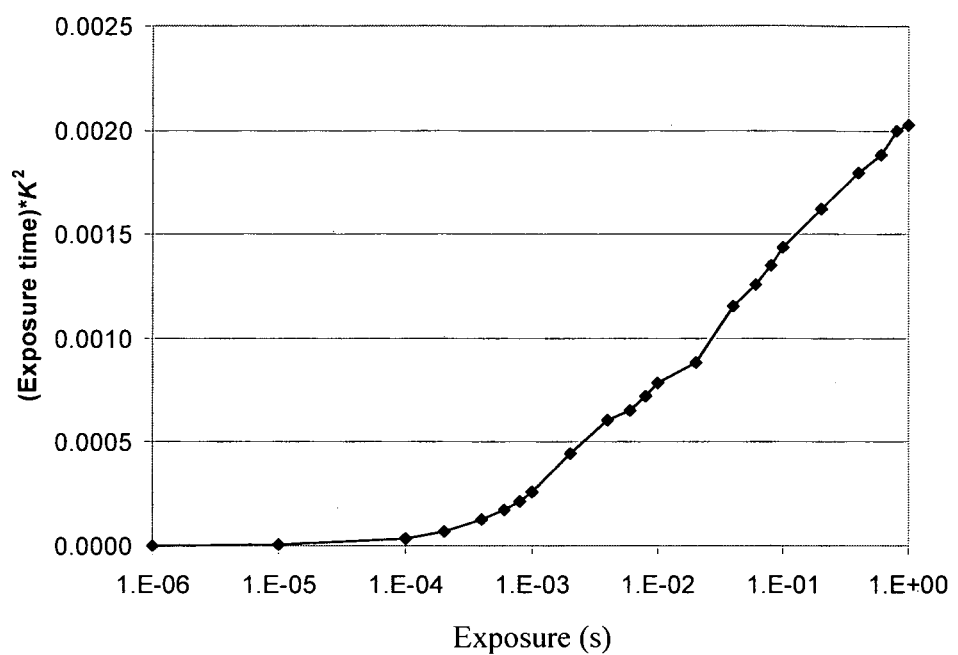
FIG. 7 illustrates data plotted in the form $TK^2$ vs. exposure time.

FIG. 7 shows the data converted into the form $TK^2$. For the analysis method above (Method 1) the slope of this function is used in equation 5. As can be seen this function has a relatively simple form.

In addition, the $R_t(T)$ data are well approximated over a wide range of time by the function $$R_t(T) = 1/(1 + T/\tau_c) \quad (6)$$

drawn in FIG. 5 as the smooth line with $\tau_c$ equal to 0.0006 s. These two observations lead to a second method of analysis (Method 2).

A simplification based on the fact that the numerically constructed autocorrelation data can be approximated by mathematical functions with adjustable parameter(s). In particular, the form in equation (6) has only one unknown parameter, $\tau_c$.

The function of equation 6 is attractive as it describes a biospeckle sample by a single time constant, and further, it is analytically integrable. This means that experimental data can be fitted to the function earlier in the analysis. Fitting data to the function earlier in the analysis is attractive because the process of differentiating experimental data can introduce noise.

Using the function of equation 6 the squared computed contrast, multiplied by the exposure time, i.e. $TK^2$ would be fitted to the integrated function $$TK^2 = K_{max}^2 \tau_c \log_e(1 + T/\tau_c) \quad 7$$

to derive a time constant $\tau_c$. Other functions than Eqn. 6 could also be used. Having derived a value of $\tau_c$ the power spectrum can be derived from the Fourier transform of Eqn. 6 and the perfusion either from moments of this transform or directly from $\tau_c$ by using a pre-computed lookup table or interpolation function.

From the power spectral density of the returning light, whether derived from the fit to a function (as given in equation 6) or computed from scaled data points, measurement of the blood flow can be made in the same way as conventional Doppler measurements and can be converted into perfusion or flow parameters.

A third method does not need multiple exposures, but builds on the knowledge gained with multiple exposures. As described above, equation (7) provides a good method for obtaining a value of $\tau_c$ by least squares fitting data collected at different exposures to this function. In the vasodilation examples (FIG. 17) this was done. A best fit value of $\tau_c$ is extracted. The fits exhibit a reasonable amount of noise. It is noted that the choice of this function means that the fitted curve always retains its shape, and can only slide left and right, without changing its slope, implying some constraints have been placed on blood cell velocities based on prior expectations.

Figure 17:
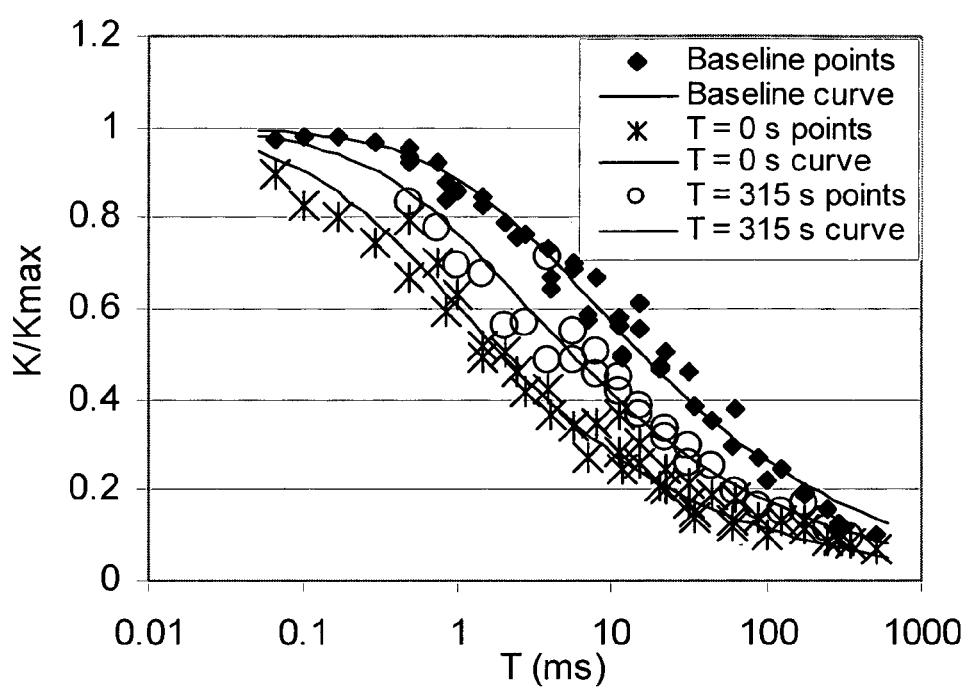
FIG. 17 is a graph of example curves from a time series of K/T curves measured after hot water-induced vasodilation.

Thus, having defined a curve such as that given by equation 6 (but not excluding others) which fits blood measurements and which has only one fit parameter $\tau_c$, mathematically, perfusion can be determined based on a single exposure T and its contrast K to calculate $\tau_c$ and define a curve such as those drawn in FIG. 17. The equivalent "graph" would be a single point with a curve "fitted" through it by shifting the curve to the left or right, although this method may be less preferred than those described above given possible noise. See FIG. 17. Nonetheless, it allows perfusion estimates using equipment that can only handle one exposure, and allows conversion of a contrast value to a suitable estimate of perfusion.

As described above a plurality of measurements with different exposure times are used. Perfusion must be as stable as possible while measurements are being taken. Provided that pulsatile flows are not an issue, and in many cases they will not be, measurements can be made in times of up to one or two seconds. To measure pulsatile flows at typical pulse rate, measurements must either be synchronized to the pulse or sampled a number of times within the pulse period. For example, measurements might be made at a rate of 10 per second, or more preferably at 30 measurements per second.

It is easier to take measurements using a diode laser of relatively high power, for example 50 mW, because this gives flexibility in either having sufficient optical power to illuminate a large area, or to obtain sufficient light at the shortest exposures. Compared to normal speckle contrast measurements, it is important that the laser does not mode-hop during exposure; mode hopping has been found to produce spurious contrast variations. In preferred embodiments a single mode laser that is thermally stabilised to avoid mode-hopping is used. An example of such a laser is the WorldStar Technologies TECRL series of diode lasers.

Generation of Contrast Images

Raw speckle images are not usually very informative, so they are converted to a contrast map or perfusion parameter format: in an apparatus according to an embodiment of the invention this is displayed with some parameter indicating contrast or movement rate at each point of the image. The usual parameter is speckle contrast K, defined as a ratio of the standard deviation of the intensity variations to the mean intensity:

$$K = \sigma_s / \langle I \rangle \quad (1)$$

Speckle contrast C is calculated over small areas of the image, usually 3×3 or 5×5 pixel squares and the results plotted as an image. A screen shot from software displaying a speckled image and the contrast computed therefrom is shown in FIG. 20). Other similar analyses, as used by Forrester et al., "A Laser Speckle Imaging Technique for Measuring Tissue Perfusion" *IEEE Transactions on Biomedical Engineering* 51:2074-2084 (2004), are also possible.

Various illuminating diode lasers were evaluated in the course of developing this system. As laser speckle is an interference effect, it is preferable to use lasers that operate reliably in a single mode, providing a coherence length longer than the expected path length differences producing the speckle pattern. In one embodiment, a temperature controlled module from WorldStarTech, with a power output of 50 mW at 658 nm, is used.

The laser illumination is expanded, using the lens supplied with the module, to provide roughly even illumination over the area of interest. Non-uniform illumination is not a problem, so long as one is not working too near the upper or lower limits of the dynamic range of the camera, as the analysis normalizes for brightness.

Images from the camera are collected and analyzed using software. FIG. 7 shows a screenshot of the prototype control and analysis software.

The various embodiments, aspects, and features of the invention described above are implemented using hardware, software, or a combination thereof and may be implemented using a computing system having one or more processors. In fact, in one embodiment, these elements are implemented using a processor-based system capable of carrying out the functionality described with respect thereto. An example processor-based system 200 is shown in FIG. 2. As shown in FIG. 1, perfusion measurement system 100 includes a digital video camera 102, an illuminating laser source 104, and a computer 200. The computer system 200 includes one or more processors, such as processor 202. The processor 202 is connected to a communication bus 222. Various software embodiments are described in terms of this example computer system. The embodiments, features and functionality of the invention as described above are not dependent on a particular computer system or processor architecture or on a particular operating system. In fact, given the instant description, it will be apparent to a person of ordinary skill in the relevant art how to implement the invention using other computer or processor systems and/or architectures.

Applications

The laser speckle imaging devices and methods of embodiments of the invention have many applications.

For example, they may be used to characterize atherosclerotic plaques. See Seemantini K., et al., Characterization of Atherosclerotic Plaques by Laser Speckle Imaging" *Circulation* 112:885-892 (2005), in which, for example, the laser speckle imaging devices and methods of embodiments of the invention will replace those devices and/or methods used therein. The laser speckle imaging devices and methods of embodiments of the invention may also be used to measure cortical vascular blood flow, the pattern of which is associated with the functional response in cerebral cortex. The pattern of the vascular blood flow can be used to study the spatiotemporal activities of the somatosensory center and the diagnosis of the focal stroke or ischemia. Using embodiments of the invention described and claimed herein allows one to obtain images of the cortical vascular blood flow pattern in which both the vessels and the blood velocity can be visualized. The laser speckle imaging devices and methods of other embodiments of the invention may also be used to measure changes in neuronal activity that are accompanied by alteration in regional cerebral blood flow. The laser speckle imaging devices and methods of embodiments of the invention may also be used to evaluate ocular blood flow, including in specific regions within the eye, particularly the retina. Particularly advantageous uses include the use to evaluate the status of blood flow or perfusion in subjects that have or are susceptible to, or suspected of having or being susceptible to, any form of macular degeneration, such as age-related macular degeneration.

The laser speckle imaging devices and methods of some embodiments of the invention may also be used for evaluating wounds, including blood flow in or around wounds, and wound bed patency. By "wound" is meant an injury to any tissue, including for example, acute, delayed or difficult to heal wounds, and chronic wounds. Examples of wounds may include both open and closed wounds. Wounds include, for example, burns, incisions, excisions, lacerations, abrasions, puncture or penetrating wounds, surgical wounds, contusions, hematomas, crushing injuries, and ulcers. Also included are wounds that do not heal at expected rates. Particularly useful is the ability to use the laser speckle imaging devices and methods according to some embodiments of the invention for measuring blood flow in chronic wounds or other delayed or hard to heal wounds. In certain embodiments the chronic wound is a diabetic ulcer, a diabetic foot ulcer, a venous ulcer, a venous stasis ulcer, a pressure ulcer, a decubitus ulcer, a vasculitic ulcer, an arterial ulcer, an infectious ulcer, a burn ulcer, a trauma-induced ulcer, or an ulceration associated with pyoderma gangrenosum, or a mixed ulcer.

In studies of tissue, local skin pathologies, or burn extent, the relative contrast between areas of skin provides useful perfusion information. Applications such as quantifying the progressive loss of circulation in the evolution of diabetes will also benefit from a more quantitative approach such as that provided herein.

In one embodiment the subject is diabetic.

In one embodiment the subject has a cardiovascular disease or condition.

Examples

The following examples are provided to illustrate speckle techniques and the practice of preferred embodiments of the instant invention, and in no way limit the scope of the invention.

Example 1

The Effects of Multiple Scatter

Relative movement of the scatterers with respect to each other can produce differences in the case of a moving solid object—a particular relative motion situation known as "triply scattered speckles" or "speckled speckles." These are speckle patterns generated in the situation where laser light is returned from a moving object to the imaging system through a stationary diffusing screen. This multiple scatter involving moving and fixed scatterers approaches the situation in biospeckle.

Figure 8:
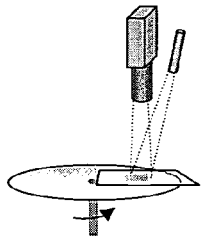
FIG. 8 illustrates a triply scattered speckle experiment in which a paper-covered wheel is rotated beneath a diffuser.
Figure 9:
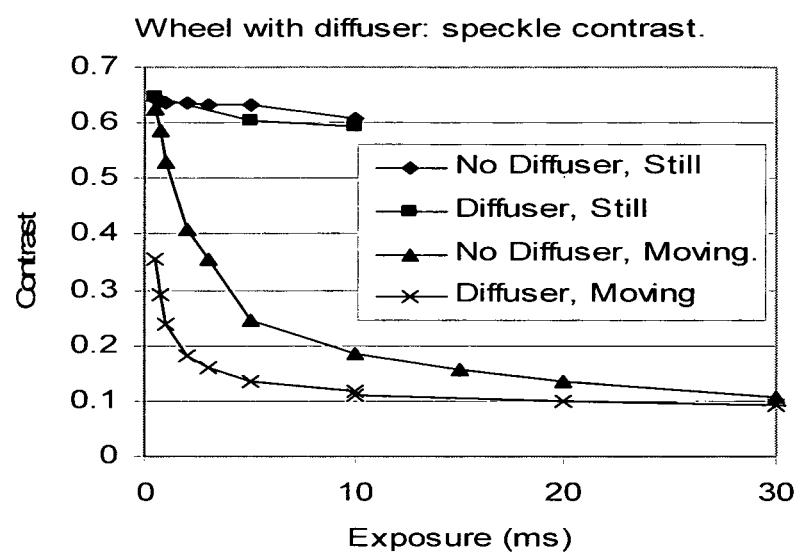
FIG. 9 illustrates the results from a triply scattered speckle experiment.

The simple experimental setup shown in FIG. 8 is an example of dynamic triply scattered speckle. A lightly diffusing plate, made of sand-blasted transparent plastic, was interposed between a paper-covered wheel and the speckle imaging system. Speckle contrast K was measured at a range of camera exposures from 0.5 to 30 ms, both with and without the diffuser in place and with the wheel either still or rotating so that the paper passed the imaging site at approximately 43 mm/s. The contrast results, plotted in FIG. 9, show the effect of the diffuser increasing the speckle fluctuation rate and hence the blurring effect at a finite exposure time. At any particular exposure below 30 ms and with the wheel rotating, the measured contrast is lower with the diffuser in place. At sufficiently long exposures the contrast in both cases approaches a common minimum level as the exposure exceeds the fluctuation time for both patterns.

Figure 10:
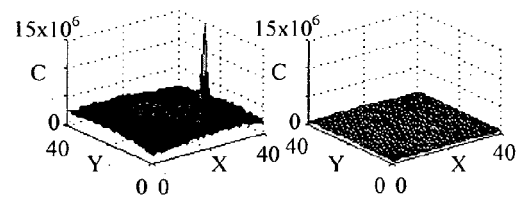
FIG. 10 shows the covariance between two frames of image speckle: LHS with no diffuser and RHS with lightly sandblasted plastic diffuser (target shifted 0.5 mm between frames; X and Y in pixels, covariance C in arbitrary units).

Watching the raw images during the wheel test, the speckle pattern appears to twinkle in place when the diffuser is in place and blur into streaks without the diffuser. This impression is supported by another simple experiment comparing static images of a paper covered surface shifted slightly between shots, both with and without the same diffuser as above. When the paper surface is shifted 0.5 mm without the diffuser in place, the speckle pattern shifts with the paper. This is confirmed by calculating the covariance between the two frames, which shows a distinct peak, displaced appropriately, as shown in FIG. 10. With the diffuser in place, the speckle pattern changes randomly when the paper is shifted, and there is no peak to the covariance between the frames. This result indicates that there is no information about the direction of movement remaining in a dynamic speckled speckle pattern. In relation to laser speckle contrast imaging of tissues, these observations show that no information about the direction of motion remains and the rate of fluctuations has no simple relation to the speed of the moving scatterer. It is this which makes the measurement of fluxes of red blood cells by speckle measurements non-trivial.

Example 2

Volume Probed by Speckle Techniques

Figure 11:
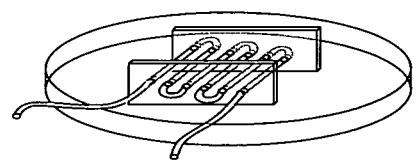
FIG. 11 illustrates a depth effect test model, consisting of flow tubes in a Petri dish to be filled with tissue phantom gel.

To evaluate depth effects using the laser speckle imaging system according to one embodiment of the invention, a model was used for capillaries near the skin surface consisting of a tissue phantom surrounding a flow tube. A tissue phantom gel consisting of 10% Intralipid, diluted 1:10 in 2% agar solution, was set in a Petri dish containing a flow tube ladder, as shown in FIG. 11, so that the surface of the tissue phantom was flush with the outside of the flow tube forming the highest rung of the ladder. The flow tube rungs of the ladder were separated by 0.4 mm vertically and 5 mm horizontally. The silicone tubing used has an internal diameter of 1.02 mm and a wall thickness of 0.57 mm.

A blood analogue was used consisting of a suspension of 6.2 μm latex beads in water, diluted to a concentration of 1% by weight, which approximate the size and concentration of red blood cells in tissue, corrected for the macroscopic size of the flow tubes compared to microscopic capillaries. This suspension was pumped through the flow tube at a fixed rate of 0.8 mm/s using a syringe pump.

Figure 12:
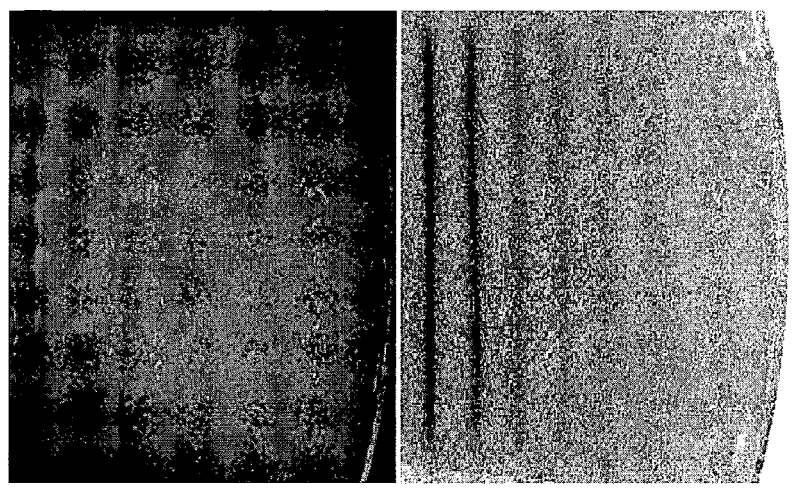
FIG. 12 shows a typical image from a depth effect test model, with a raw image on the left and a speckle contrast image on the right.
Figure 13:
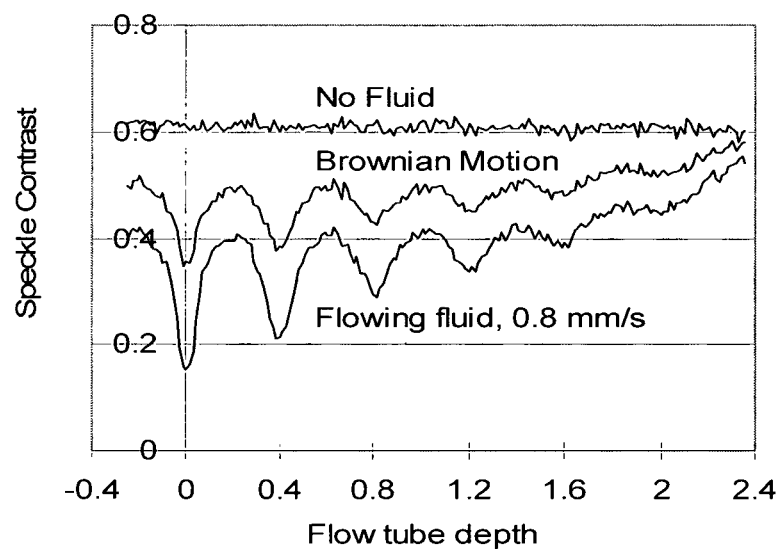
FIG. 13 is a graphical illustration of one example of depth effect results.

FIG. 12 shows a typical speckle image and the related speckle contrast image of this model using the laser speckle imaging system of one embodiment of the invention. Taking the mean of each image column in the central part of the image produces a plot, FIG. 13, showing by the depth of the troughs the effect of increasing tissue phantom depth on the flow-induced speckle contrast reduction. The contrast reduction effect falls off with increasing depth, such that in this plot the sixth tube at 2 mm depth is only barely detectable as a slight depression of the curve.

This plot also shows the effect of Brownian motion: contrast declines when fluid is introduced even when there is no net flow through the tube. The mean kinetic energy of the particles at a particular temperature and hence the root-mean-square velocity, is given by the equation:

$$\frac{1}{2}m\overline{v^2} = \frac{3}{2}kt \qquad (3)$$

The rms velocity of the latex particles due to Brownian motion at room temperature is approximately 0.3 mm/s, sufficiently large when compared to the detectable flow rates that there should be a measurable contrast reduction effect. The Brownian motion is apparent using speckle techniques in fluids containing particle scatterers such as cross-linking polymers, paints and resins but Brownian motion was not observed in vitro in muscle tissue.

Figure 14:
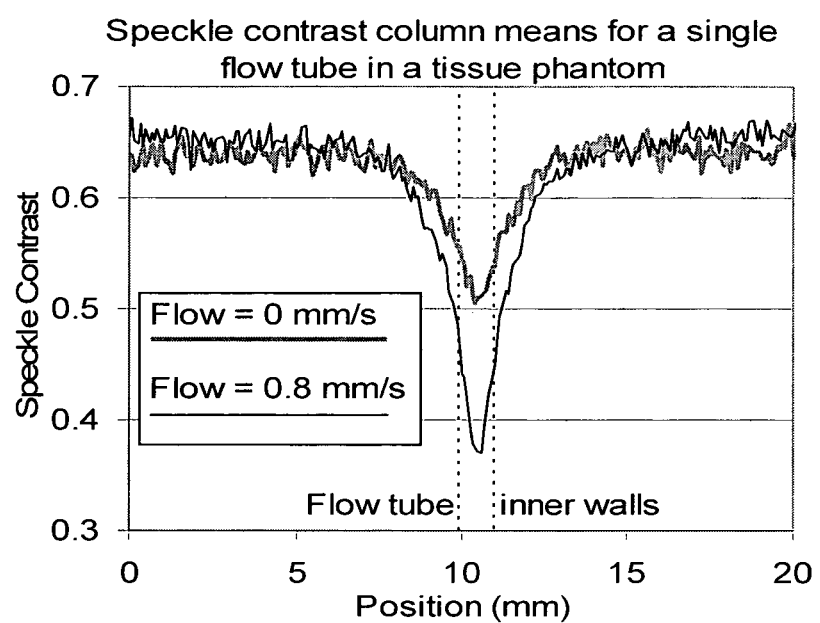
FIG. 14 is a graphical illustration of the extent of blurring due to multiple scatter.

The contrast between the tube positions falls proportionally to the contrast at tube positions when fluid is present or flowing in the tube, indicating that a multiple scattering effect extends the blurring influence of the moving scatterers to an extended volume of the tissue phantom. FIG. 14 is a speckle contrast image of a single flow tube embedded in the same phantom mixture described above at 1 mm depth below the phantom surface. The contrast reduction effect of the fluid movement extends significantly beyond the walls of the tube.

Figure 15:
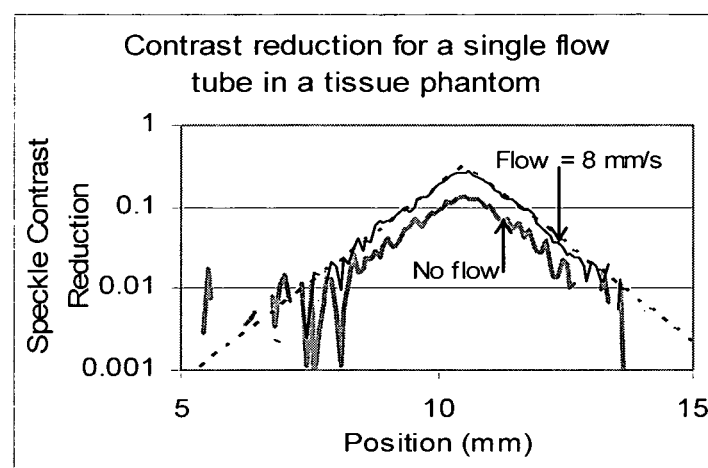
FIG. 15 illustrates the contrast reduction effect of a single flow tube on a semi-log scale.

Taking the difference between the mean contrast for the tissue phantom with no fluid present and the contrast of the blurred image, one can determine the movement-related contrast reduction. This value, plotted in FIG. 15, falls exponentially with distance from the tube, with a scale length λ determined by the depth of the phantom and the phantom optical characteristics. The distance λ over which the blurring effect falls to 1/e of its value increases with the depth of the tube in the phantom and with the concentration of scatterers in the phantom. This distance is expected to be wavelength dependant in tissue and offers a method of controlling the tissue volume sampled using embodiments of the invention.

Example 3

Perforators

The capillaries that supply the skin are fed from deeper vessels by perforators: arterioles that come to the surface from deeper vessels. Locating these perforators is often important for planning various reconstructive surgical procedures. They are currently generally located using an ultrasound Doppler flowmetry probe. This is a single point method and it can thus be improved by using a full-field image method in accordance with an embodiment of the present speckle contrast imaging invention.

Figure 16:
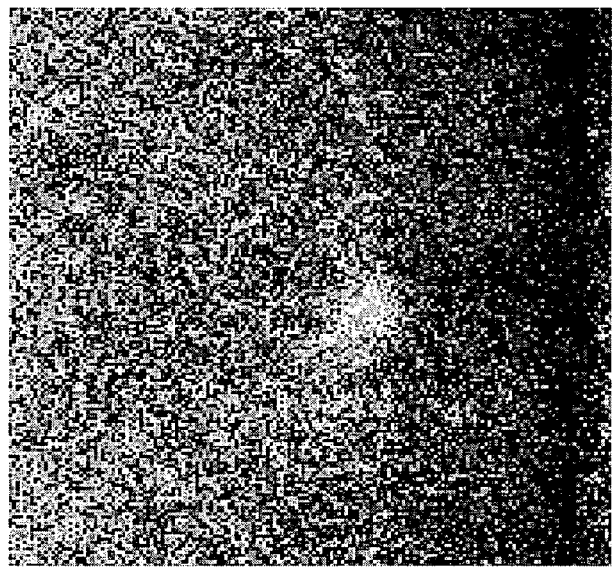
FIG. 16 illustrates the pulsatile component of the contrast reduction effect, showing a perforator on the forearm.

In this Example, effort was made to identify perforators by finding regions of pulsatile flow, where the pulse is more evident in those capillaries closest to the arterial perforator. Searching along the forearm using the live speckle contrast display yielded a possible candidate point for a perforator, as the contrast fluctuated at the pulse rate. Taking the time domain Fourier transform at each point of the contrast image and then plotting the amplitude at each point of the Fourier component corresponding to the pulse rate produced FIG. 16, an image of the pulsatile component of the contrast reduction effect. The location of the forearm perforator shows up clearly as shown in FIG. 16. This location was confirmed using Doppler ultrasound flowmetry.

Example 4

Measurement of Perfusion Change

As a test of the second method of analysis described above, using the parametric autocorrelation function (Eqn. 6), a time series of contrast versus exposure time curves were measured on the back of the hand after inducing vasodilation using hot water. FIG. 17 shows three example curves from the data set. The baseline curve is the initial state, with the "Time=0 s" curve measured as soon as possible after inducing vasodilation.

In the analysis of method 1, a curve was fitted by eye to smooth the K vs. T data and extracted a differential curve (Equation 5) representing the autocorrelation function, which approximated an analytic function. Given data that can generally be represented by this function, method 2 avoids numerical differentiation by integrating the analytic function (6), and equating that to the integral of Equation (5), which is the measured data set, i.e.

$$\frac{TK^2}{K_{max}^2} = \tau_c \log(1 + T/\tau_c) \qquad (7)$$

or, solving for $K/K_{max}$:

$$\frac{K}{K_{max}} = \sqrt{\frac{\tau_c}{T}\log(1 + T/\tau_c)} \qquad (8)$$

Values of $\tau_c$ may then be found by least-squares fitting. The resulting fitted curves for the three example series, shown in FIG. 17, fit the data satisfactorily, justifying the choice of function and this method of analysis.

Figure 18:
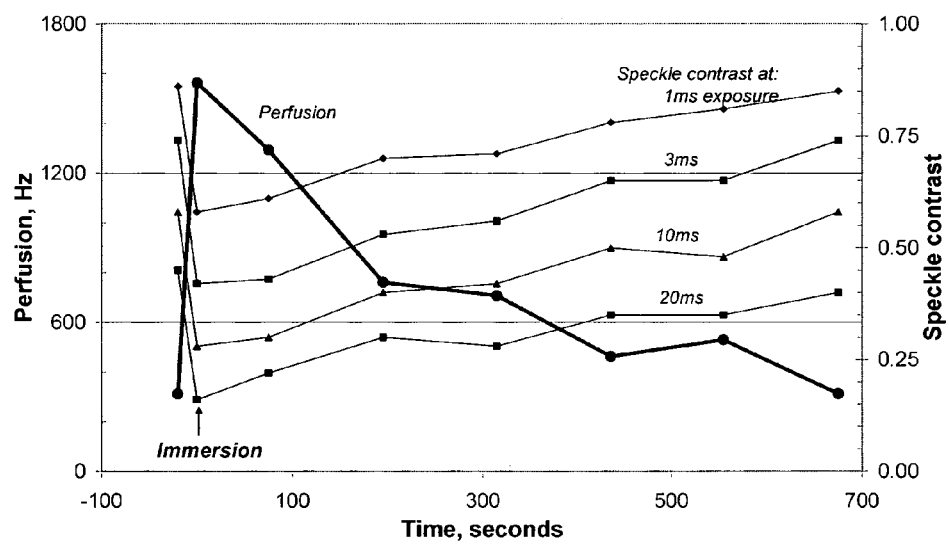
FIG. 18 illustrates perfusion index and speckle contrast changes in the back of the hand after hot water-induced vasodilation.

Using the $\tau_c$ values derived from each of 8 contrast vs. exposure time curves, autocovariance functions and power spectral densities were produced. The first moment of the power spectral density—proportional to the perfusion and called "perfusion index"—at each measurement time was calculated, and is shown in FIG. 18. The perfusion, measured in units of Hertz, which in accordance with the theory underlying Doppler instruments is directly proportional to the tissue perfusion measured in milliliters of blood per gram of tissue, rises by a factor of 5 immediately following the immersion, and recovers to its pre-challenge value over a period of approximately 10 minutes.

The Figure also shows calculated values of speckle contrast at selected exposure times during this event. At any particular time, all such contrast information is used to compute the perfusion. If as is conventionally done, only one exposure is used, a relative recovery of the perfusion back to normal can be deduced from the changing value of speckle contrast at that exposure. Quantification, though, is not possible. For example, a speckle contrast of 0.5 is reached after 130 seconds using 3 ms exposures, but not until 430 seconds using 10 ms. At these times, the true perfusion differs by a factor of two. An empirical calibration would be required if contrast values at one single exposure time were used. But the calibration must implicitly assume that the contrast will change by a certain amount if the exposure is changed. This is equivalent to assuming that all subjects have the same red cell speed distribution. The method disclosed herein does not need to make this assumption. The perfusion is not linearly related to the contrast measurements—the contrast measurements rise at a nearly constant rate following immersion, while the perfusion index falls on a non-linear curve.

With no further analysis, FIG. 18 shows that most individual speckle fluctuations (and by implication, Doppler periods) lie between about 0.3 and 30 ms. It is over this range that time-averaging produces the most reduction in contrast. Maximum contrast reduction corresponds to removing frequencies around 500 Hz, a value near the first moment of the power spectrum here. A simple interpretation is that this corresponds to scattering particle speeds of the order of only 0.1 mm/s, considerably lower than the 1 mm/s expected in capillaries. Most of the power is shifted to lower frequencies (30-500 Hz) than expected because, due to the angular dependence of scatter by blood cells, the chance of experiencing a collision resulting in a high Doppler shift is low. Most scattering events only intercept a small component of particle velocity.

Example 5

Dermal Pulse

Figure 19:
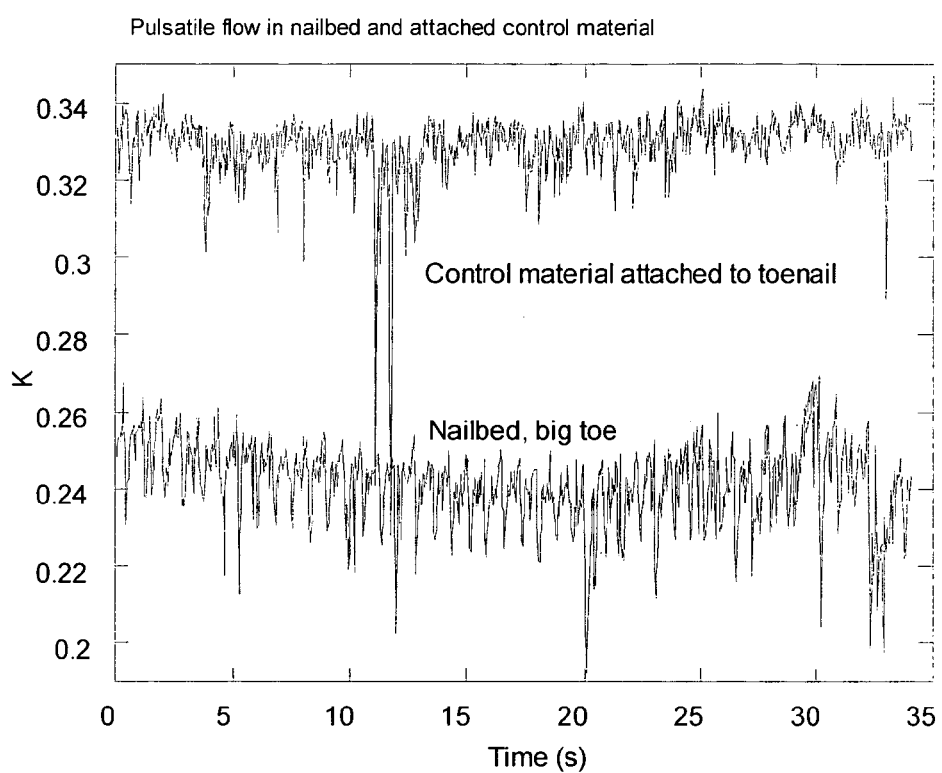
FIG. 19 illustrates a time series measurement of contrast, showing pulse.

Experiments show that time series measurements of speckle contrast exhibit fluctuations in blood flow additional to the localized perforator effect of Example 3. A natural fluctuation to look for is pulse, and contrast reduction in time with the pulse can be detected in a variety of areas, including the back of the hand, inner wrist, upper forearm and fingertip and nailbed. FIG. 19 shows a time series measurement of the speckle contrast of the nailbed, clearly showing the pulse. Obscuring targets (e.g. opaque tape) attached firmly to the tissue showed no regular fluctuation, confirming that the pulse effect seen is a result of flow in the capillaries rather than gross movement of the tissue with heartbeat. Other experiments (e.g. those in Example 2) show that the light does not penetrate beyond 1 to 2 mm depth so that the fluctuations are not related to deeper vessels.

The record shown is that of speckle contrast, but as illustrated in Example 4, such records could be converted by the method of one embodiment of the invention to actual perfusion values within the capillary structure of the dermis.

The present invention is not limited by any particular preferred embodiments. It will occur to those ordinarily skilled in the art that various modifications may be made to the disclosed embodiments without diverting from the concept of the inventions. All such modifications are intended to be within the scope of the present invention.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims accorded their full range of equivalents.

The specific methods and compositions described herein are representative of certain preferred embodiments and are exemplary and not intended as limitations on the scope of the invention. Other objects, aspects, and embodiments will occur to those in the art upon consideration of this specification, and are encompassed within the spirit of the invention as defined by the scope of the claims. It will be readily apparent to one skilled in the art that varying substitutions and modifications may be made to the embodiments of the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of an embodiment of the invention are described in terms of Markush groups (claiming alternatives), it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement has been specifically and without qualification or reservation expressly adopted in a responsive writing by Applicants.

The invention claimed is:

1. A method of measuring perfusion in tissue, which comprises the steps of:
    a) producing a series of optical images of the tissue under laser light by performing the following steps until a full exposure range is covered:
        1) producing an optical image of the tissue with a preselected exposure time with an optical imaging device;
        2) adjusting the preselected exposure time of the optical imaging device; and then
        3) repeating steps 1) and 2);
    b) calculating a series of contrast images based on said optical images of the tissue;
    c) when the full exposure range is covered, determining a power spectrum of scattered light by generating a temporal autocorrelation function from the change of spatial contrast of the series of contrast images with exposure time at points of interest;
    d) converting the temporal autocorrelation function to its power spectrum; and then
    e) determining perfusion from the power spectrum.

2. A method according to claim 1, wherein the tissue is skin.

3. A method according to claim 1, wherein the tissue is diabetic human skin.

4. A method of measuring perfusion in tissue, which comprises the steps of:
    a) producing a series of optical images of the tissue under laser light by performing the following steps until a full exposure range is covered:
        1) producing an optical image of the tissue with a preselected exposure time with an optical imaging device;
        2) adjusting the preselected exposure time of the optical imaging device; and then
        3) repeating steps 1 and 2;
    when the full exposure range is covered, calculating contrast data from the series of optical images of the tissue representing the variation of contrast with exposure time at each pixel of interest; and
    b) generating a representative 3-D matrix
    c) determining one or more parameters of a temporal autocorrelation function which fits the contrast data at each pixel of interest from the 3-D matrix; and then
    d) calculating the perfusion from the one or more parameters.

5. A method according to claim 4, wherein the tissue is skin.

6. A method according to claim 4, wherein the tissue is diabetic human skin.

7. An apparatus for measuring perfusion in tissue, which comprises a digital video camera, a laser light source, and a processor arranged to operate the laser light source and camera to:
    a) produce a series of optical images of the tissue under the laser light source by performing the following steps until a full exposure range is covered:
        1) receive an optical image from the camera with a preselected exposure time;
        2) adjust the preselected exposure time of the camera; and then
        3) repeat steps 1) and 2);
    b) calculate a series of contract images based on said optical images of the tissue;

c) when the full exposure range is covered, determine a power spectrum of scattered light by generating a temporal autocorrelation function from the change of spatial contrast of the series of contrast images with exposure time at points of interest;
d) convert the temporal autocorrelation function to its power spectrum; and then
e) determine perfusion from the power spectrum.

8. An apparatus for measuring perfusion in tissue, which comprises a digital video camera, a laser light source, and a processor arranged to operate the laser light source and camera to:
a) produce a series of optical images of the tissue under the laser light source by performing the following steps until a full exposure range is covered;
   1) receive an optical image from the camera with a preselected exposure time;
   2) adjust the preselected exposure time of the camera; and then
   3) repeat steps 1 and 2;
when the full exposure range is covered, calculate contrast data from the series of optical images of the tissue representing the variation of contrast with exposure time at each pixel of interest;
b) generate a representative 3-D matrix;
c) determine one or more parameters of a temporal autocorrelation function which fits the contrast data at each pixel of interest from the 3-D matrix; and then
d) calculate the perfusion from the one or more parameters.

9. A method for ascertaining particulate flow in a vessel, the method comprising the steps of:
a) directing coherent illuminating radiation to illuminate particulates within the vessel, the illuminating radiation being of a wavelength or wavelength band substantially in the visible to near infra-red light region of the spectrum;
b) imaging different optical speckle patterns of the illuminated particulates within the vessel using an image capture device to produce a series of optical speckle pattern images by performing the following steps until a full exposure range is covered:
   1) producing an optical speckle pattern image of the illuminated particles within the vessel with a preselected exposure time with an optical imaging device;
   2) adjusting the preselected exposure time of the optical imaging device; and then
   3) repeating steps 1) and 2);
c) when the full exposure range is covered, processing data from the series of optical speckle pattern images to determine a power spectrum of scattered light from the series of optical speckle pattern images by generating a temporal autocorrelation function from the change of spatial contrast of the series of optical speckle images with exposure time at points of interest;
d) converting the temporal autocorrelation function to its power spectrum; and then
e) ascertaining the flow of particulates within the vessel based on the power spectrum.

10. A method for ascertaining particulate flow in a vessel, the method comprising steps of:
a) directing coherent illuminating radiation to illuminate particulates within the vessel, the illuminating radiation being of a wavelength or wavelength band substantially in the visible to near infra-red light region of the spectrum;
b) imaging different optical speckle patterns of the illuminated particulates within the vessel using an image capture device to produce a series of optical speckle pattern images by performing the following steps until a full exposure range is covered:
   1) producing an optical speckle pattern image of the illuminated particles within the vessel with a preselected exposure time with an optical imaging device;
   2) adjusting the preselected exposure time of the optical imaging device; and then
   3) repeating steps 1) and 2);
when the full exposure range is covered, processing data from the series of optical speckle pattern images by calculating contrast data from the series of optical speckle pattern images representing the variation of contrast with exposure time at each pixel of interest;
c) generating a representative 3-D matrix;
d) determining one or more parameters of a temporal autocorrelation function which fits the contrast image data at each pixel of interest from the 3-D matrix; and then
e) calculating from the one or more parameters the flow of particulates within the vessel.

11. A method according to claim 9 or 10, wherein the illumination radiation delivered is a beam of laser light.

12. A method according to claim 9, wherein the vessel is a blood vessel within a body part of a subject.

13. A method according to claim 9, wherein the body part is skin.

14. A method according to claim 9, wherein the flow of particulates within the vessel provides a measurement of blood flow.

15. A method according to claim 9, wherein the flow of particulates within the vessel provides a measurement of tissue perfusion.

16. A method according to claim 9, wherein the flow of particulates within the vessel provides a measurement of tissue ischemia.

17. A method according to claim 9, wherein the flow of particulates within the vessel provides a measurement of inflammation.

18. A method according to claim 9, wherein the subject has diabetes.

19. A method according to claim 9, wherein the subject body part is skin that has been burned.

20. A method according to claim 10, wherein the vessel is a blood vessel within a body part of a subject.

21. A method according to claim 10, wherein the body part is skin.

22. A method according to claim 10, wherein the flow of particulates within the vessel provides a measurement of blood flow.

23. A method according to claim 10, wherein the flow of particulates within the vessel provides a measurement of tissue perfusion.

24. A method according to claim 10, wherein the flow of particulates within the vessel provides a measurement of tissue ischemia.

25. A method according to claim 10, wherein the flow of particulates within the vessel provides a measurement of inflammation.

26. A method according to claim 10, wherein the subject has diabetes.

27. A method according to claim 10, wherein the subject body part is skin that has been burned.

28. A method according to claim 1 wherein step b) of calculating a series of contrast images based on the said optical images of the tissue comprises progressively calculating each contrast image in the series during step a) after each optical image s produced.

29. An apparatus according to claim 7 wherein the processor is arranged in b) to calculate the series of contrast images based on said optical images of the tissue by progressively calculating each contrast image in the series during a) after receiving an optical image from the camera.

\* \* \* \* \*